United States Patent [19]

Ropars et al.

[11] Patent Number: 4,752,586
[45] Date of Patent: Jun. 21, 1988

[54] APPARATUS FOR ENCAPSULATING BIOLOGICAL ACTIVE SUBSTANCES INTO ERYTHROCYTES

[75] Inventors: Claude Ropars, Tours; Yves Nicolau, La Chapelle St Mesmin; Maurice Chassaigne, St Cyr S. Loire, all of France

[73] Assignees: Centre National de la Recherche Scientifique, Paris; Centre Hospitalier Regional de Tours, Tours, both of France; Studiengesellschaft Kohle mbH, Mulheim/Ruhr, Fed. Rep. of Germany

[21] Appl. No.: 933,008

[22] Filed: Nov. 20, 1986

Related U.S. Application Data

[60] Division of Ser. No. 546,015, Oct. 27, 1983, Pat. No. 4,652,449, which is a continuation-in-part of Ser. No. 470,817, Feb. 28, 1983, abandoned.

[30] Foreign Application Priority Data

Jul. 5, 1982 [FR] France .................. 82 11749

[51] Int. Cl.⁴ .............................. C12M 1/00
[52] U.S. Cl. ................................ 435/287; 435/2; 435/316; 210/321.72
[58] Field of Search ............... 435/2, 287, 311, 316; 210/321.1, 321.2, 321.3, 645; 604/4, 6

[56] References Cited

U.S. PATENT DOCUMENTS

| | | | |
|---|---|---|---|
| 2,461,505 | 2/1949 | Daniel | 210/645 |
| 3,591,493 | 7/1971 | Zeimeh | 210/645 |
| 4,153,684 | 5/1979 | Audibert et al. | 424/88 |
| 4,158,052 | 6/1979 | Audibert et al. | 424/45 |
| 4,186,194 | 1/1980 | Adam et al. | 424/89 |
| 4,192,869 | 3/1980 | Nicolau et al. | 424/199 |
| 4,235,771 | 11/1980 | Adam et al. | 260/112.5 R |
| 4,241,187 | 12/1980 | White | 435/285 |
| 4,272,524 | 6/1981 | Chedid et al. | 424/177 |
| 4,289,756 | 9/1981 | Zimmerman et al. | 424/101 |
| 4,321,259 | 3/1982 | Nicolau et al. | 424/101 |
| 4,323,559 | 4/1982 | Audibert et al. | 424/177 |
| 4,327,085 | 4/1982 | Audibert et al. | 424/177 |
| 4,366,176 | 12/1982 | Wetzel | 426/104 |
| 4,370,265 | 1/1983 | Adam et al. | 260/112.5 R |
| 4,473,563 | 9/1984 | Nicolau et al. | 424/224 |
| 4,478,824 | 10/1984 | Franco et al. | 424/101 |
| 4,517,080 | 5/1985 | Deloach et al. | 210/321.1 |

FOREIGN PATENT DOCUMENTS

| | | |
|---|---|---|
| 0001104 | 3/1979 | European Pat. Off. |
| 2288527 | 5/1976 | France |
| 2292486 | 6/1976 | France |
| 2324311 | 4/1977 | France |
| 2343483 | 10/1977 | France |
| 2355505 | 1/1978 | France |
| 2369292 | 5/1978 | France |
| 2428051 | 12/1981 | France |

OTHER PUBLICATIONS

Martin et al.,-Harper's Review of Biochemistry-19th edit., pp. 68, 163, 164, 180, 182, 190, 214, 215, 217, 241, 252 & 255.
Ropars-Bellagio Symposium—1st Int. Conf. on Red Blood Cell Carriers (1984), pp. 33–43.

Primary Examiner—Samuel Scott
Assistant Examiner—Noah Kamen
Attorney, Agent, or Firm—Sprung Horn Kramer & Woods

[57] ABSTRACT

This invention relates to a process for the encapsulation in human or animal erythrocytes of at least one substance having a biological activity, characterized in that the primary compartment of at least one dialysis element is continuously supplied with an aqueous suspension of erythrocytes, the secondary compartment of the dialysis element contains an aqueous solution which is hypotonic with respect to the erythrocyte suspension in order to lyse the erythrocytes, the erythrocyte lysate is in contact with said substance having a biological activity and, in order to reseal the membrane of the erythrocytes, the osmotic and/or oncotic pressure of the erythrocyte lysate is increased after it has been brought into contact with said substance having a biological activity.

10 Claims, 15 Drawing Sheets

FIG_1

FIG_3

FIG_4

FIG_5

FIG_6

FIG_7

FIG_8

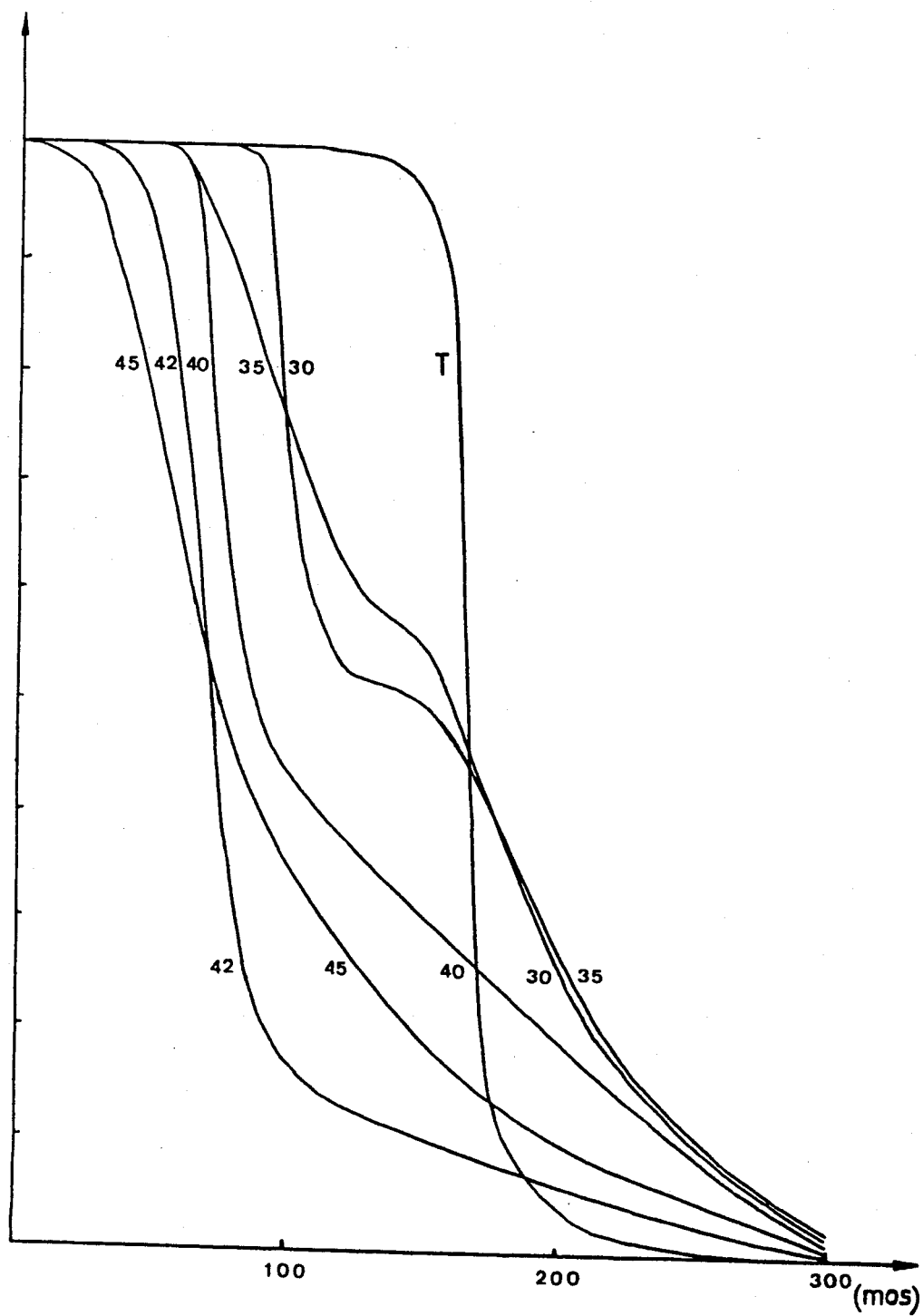
FIG_10

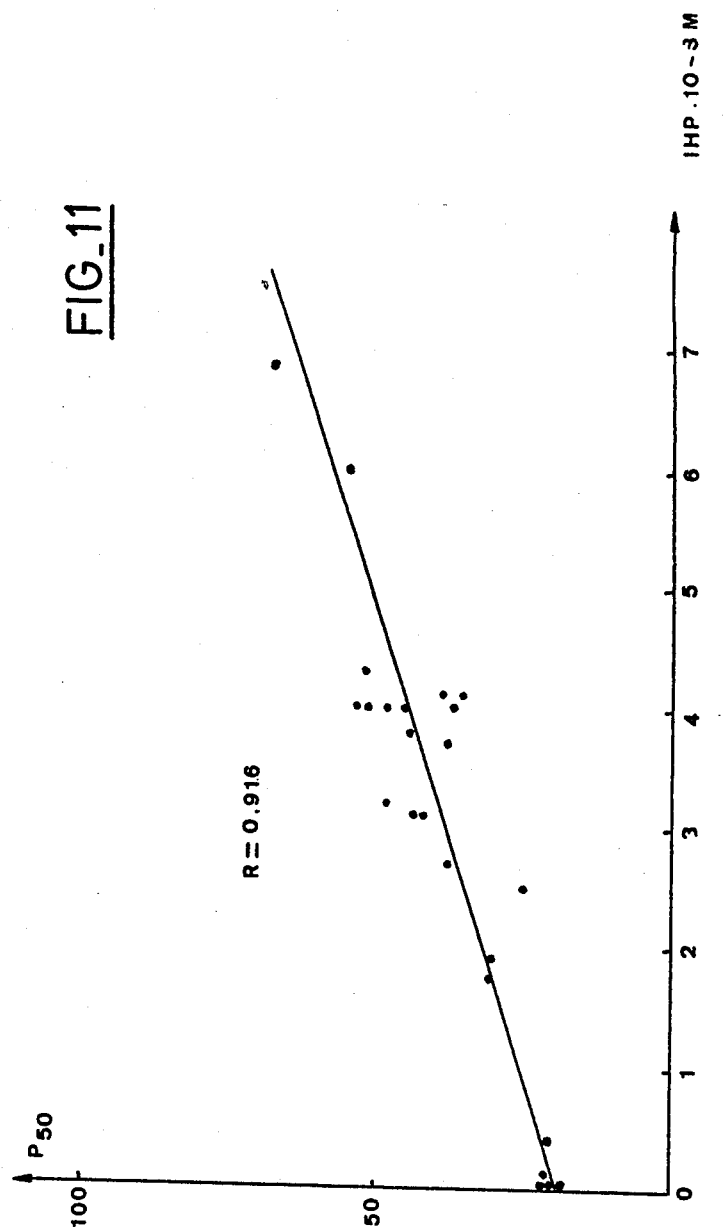
FIG_11

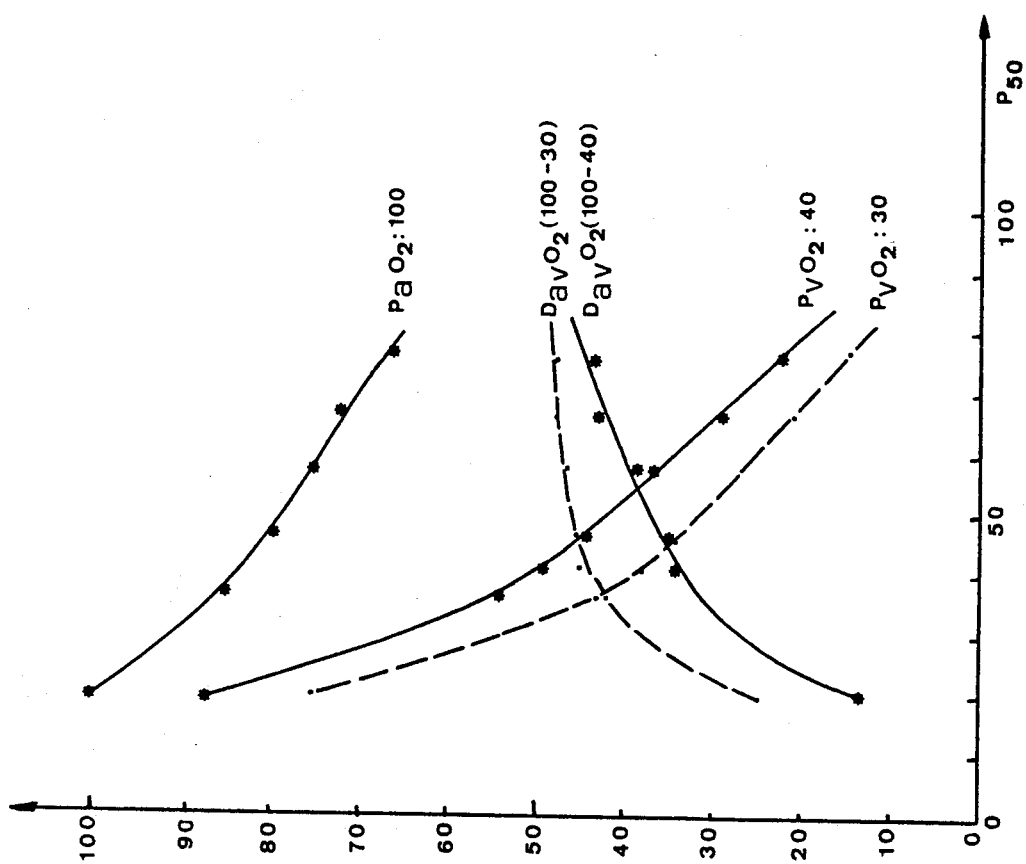
FIG._12

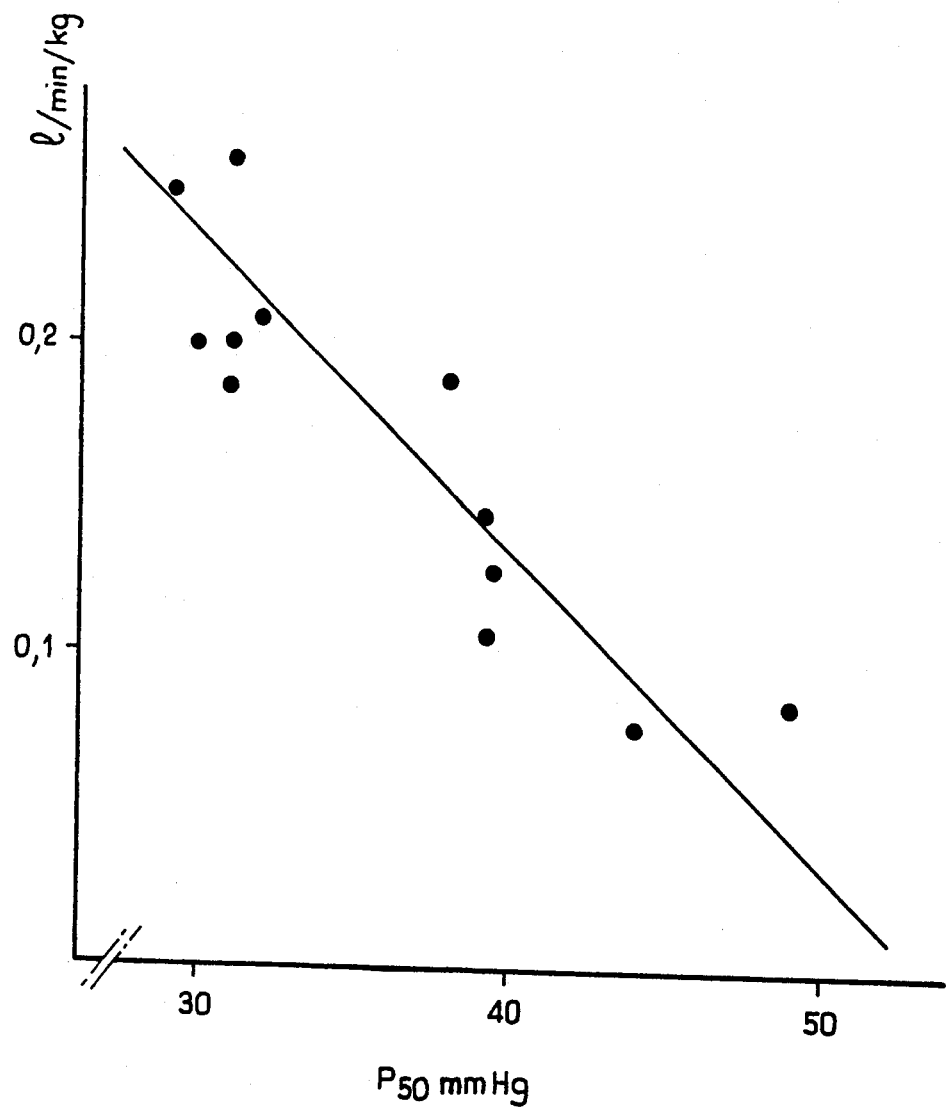
FIG_13

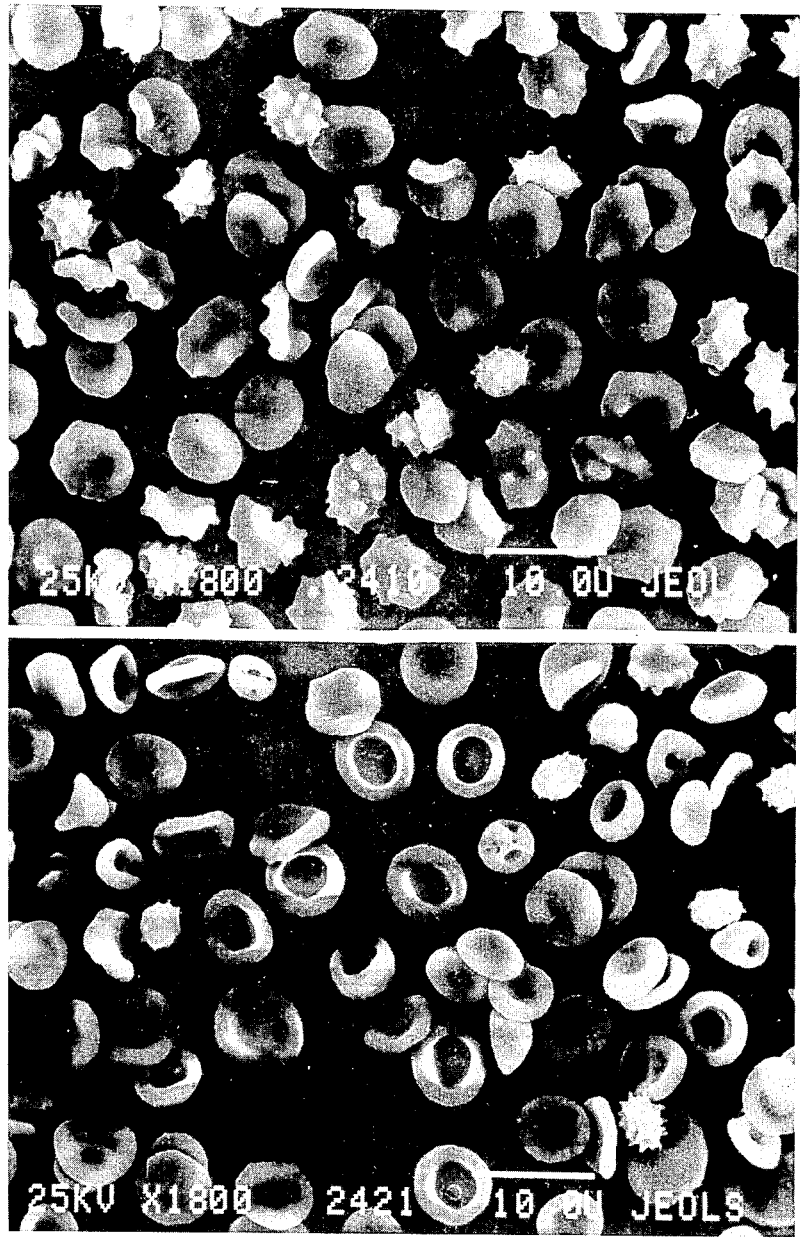
FIG_14

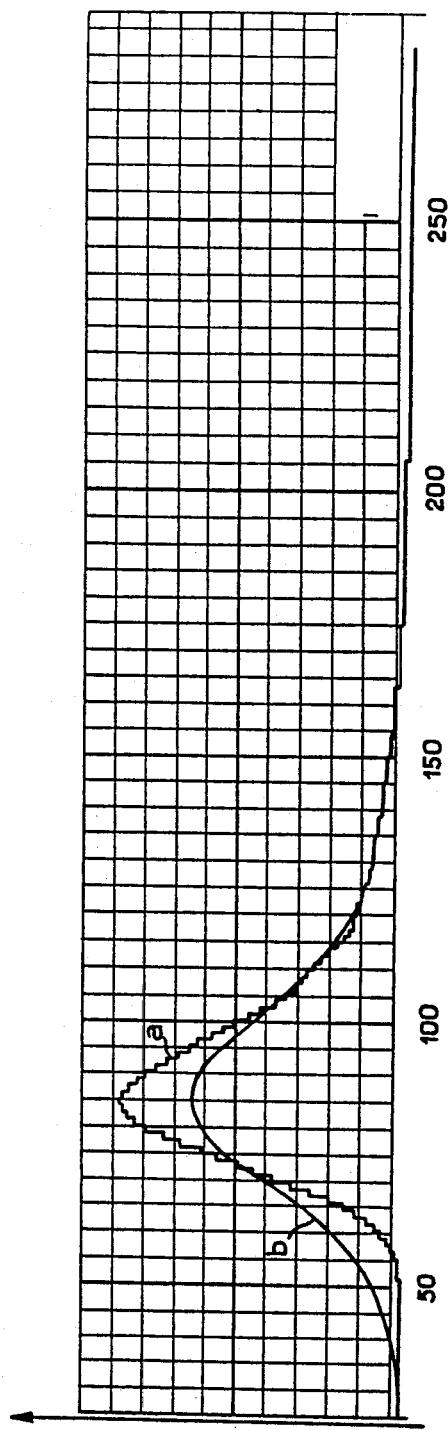
FIG._15

APPARATUS FOR ENCAPSULATING BIOLOGICAL ACTIVE SUBSTANCES INTO ERYTHROCYTES

This is a division of application Ser. No. 546,015, filed Oct. 27, 1983, now U.S. Pat. No. 4,652,449, which is a continuation-in-part of Ser. No. 470,817, Feb. 28, 1983, abandoned.

BACKGROUND OF THE INVENTION

1. Field of the Invention

This invention which was realized in collaboration with the CENTRE NATIONAL DE LA RECHERCHE SCIENTIFIQUE, the CENTRE REGIONAL DE TRANSFUSION SANGUINE represented by the CENTRE HOSPITALIER REGIONAL DE TOURS, and the STUDIENGESELLSCHAFT KOHLE mbH, relates to a process for the encapsulation in human or animal erythrocytes of at least one substance having a biological activity, to an apparatus which may be used for carrying out this process and to the erythrocytes which are obtained.

BACKGROUND INFORMATION

Before describing the present invention, it may be advantageous to recall some concepts of the subject matter.

Blood is a complex mixture consisting of a liquid, the plasma, in which are suspended red cells (erythrocytes) which transport oxygen, white cells (leucocytes) and platelets. The plasma contains solubilized soluble metabolites, proteins and salts which are exchanged in the different tissues.

Only erythrocytes are of interest within the scope of the present invention.

In a simplified manner, it may be considered that erythrocytes consist of a membrane which surrounds a cytoplasm which is essentially filled with haemoglobin.

The function of haemoglobin is to combine with molecular oxygen during the passage of the erythrocytes through the lungs and to transport this oxygen to all the tissues of the body for it to be used there.

Like every cell, erythrocytes may be lysed under certain conditions, in particular under osmotic pressure conditions In 1952, Teorrel introduced the concept of erythrocyte membrane resealing, i.e., the reconstitution of the erythrocyte membrane after lysis of the erythrocytes.

Thus, insofar as it was possible to open and close erythrocytes, it should therefore be possible to introduce certain exogeneous components into the erythrocytes. In addition to the basic technique which comprises introducing the erythrocytes into a solution contained in a recipient the osmotic pressure of which is successively changed to effect lysis, then resealing, some other processes should be mentioned which effect lysis in an iso-osmotic medium by applying an electric or thermal shock to the erythrocytes. In some cases, viruses or viral proteins have also been used to perform this encapsulation.

Encapsulations have also been performed by dialysis in a cellophane bag. All the processes which have previously been carried out have the common disadvantage of producing small encapsulation yields, of being extremely chancy with respect to their reproducibility and of only allowing the treatment of small quantities of erythrocyte suspensions.

Thus, although encapsulation has been reported of some enzymes, of the IX factor, of desferrioxamine, of organic acids, of glucose, of saccharose, of the A fragment of the diphtheric anti-toxin and of methothrexate, these processes have remained at the laboratory stage and it is still impossible for them to be applied to man.

It is only a recent publication by Green R. et al. (The Lancet (1980), Aug. 16th, 327–330) which describes the Desferal ® (Ciba-Geigy) encapsulation and the use of the resulting erythrocytes in man.

However, having been produced by simple dilution in a hypo-osmotic medium, this encapsulation provides very low incorporation yields of Desferal in the erythrocytes.

For this reason, the object of the present invention is to perfect a process and an apparatus which allow the very high yield encapsulation in erythrocytes of substances which have a biological activity, and allow large quantities of erythrocyte suspensions to be treated while ensuring the maintenance of good sterility conditions which permit the use of erythrocytes thus obtained in man or animals.

Although the present invention has been developed for the encapsulation of a large number of compounds having a biological acitivity, one of the classes of compounds of a biological activity appears to be of more particular interest. This class embraces allosteric effectors of haemoglobin.

At the stage of the lungs, haemoglobin forms with oxygen a reversible addition product: oxyhaemoglobin.

This addition product decomposes at the level of the capillary system to release oxygen, because the partial pressure of oxygen in the capillary system is lower (about 70 mm of Hg) than in the lungs (about 100 mm of Hg).

Under normal conditions, only some, about 25% of the haemoglobin dissociates, and the remainder returns to the lungs through the venous system.

In vitro, it has been possible to show the function of some substances, such as inositol hexaphosphate (IHP), and pyridoxal phosphate for example, which are capable of combining with haemoglobin at the binding site of 2,3-diphosphoglycerate.

These products which are termed "allosteric effectors of haemoglobin" (AEH) modify the allosteric conformation of haemoglobin, the effect of which is to reduce the affinity of haemoglobin for oxygen.

A reduction in the affinity of haemoglobin for oxygen facilitates the release of oxygen from oxyhaemoglobin, even for relatively elevated oxygen partial pressures.

Under these conditions, without the total oxygen content of the blood being notably modified, it is possible to envisage increasing the oxygen release capacity of the blood to the tissues by using red blood cells containing a modified haemoglobin.

This type of treatment of haemoglobin permits an improved oxygenation of the tissue by improving the release of oxygen.

The uses of these allosteric effectors of haemoglobin are potentially numerous, for example in the treatment of certain situations of hypoxy.

They may improve or accelerate certain therapeutic processes, for example in the prevention of heart infarction due to ischaemia, or they can modify the respiratory physiology at increased altitudes or low depth.

Of course, the essential problem is to bring the effectors in situ so that they may become attached to the intracellular haemoglobin.

Attempts at transforming haemoglobin in solution by allosteric effectors of haemoglobin have been carried out in vitro, but practical applications are still incapable of a therapeutic use due to the inadequate life span of haemoglobin in solution and to the reduced properties which it then has in transporting oxygen.

U.S. Pat. No. 4,192,869 and European Patent No. 0,001,104 describe processes which transform red blood cells by an interaction of said blood cells with liposomes loaded with allosteric effectors of haemoglobin, in particular IHP (inositol hexaphosphate).

SUMMARY OF THE INVENTION

The process and apparatus according to the present invention allow the transformation of haemoglobin under conditions which allow its use on a therapeutic level, using an allosteric effector of haemoglobin as a compound having a biological activity.

In order to achieve this, the present invention proposes a process for the encapsulation in human or animal erythrocytes of at least one substance having a biological activity, characterised in that the primary compartment of at least one dialysis element is continuously supplied with an aqueous suspension of erythrocytes, the secondary compartment of this dialysis element contains an aqueous solution which is hypotonic with respect to the erythrocyte suspension in order to lyse the erythrocytes, and in that the erythrocyte lysate is then in contact with said substance of a biological activity, and in that, in order to reseal the membrane of the erythrocytes, the osmotic and/or oncotic pressure of the erythrocyte lysate is increased after it has been brought into contact with said substance having a biological activity, and in that the suspension of resealed erythrocytes is recovered.

Within the context of the present invention, the term "dialysis element" will generally be understood as an element comprising two compartments which are separated by a dialysis membrane through which an ionic exchange may take place which allows the osmotic pressure of an aqueous solution in one of the compartments to be modified in a controlled manner by introducing an aqueous solution of a salt into the other compartment. This type of dialysis element is widely used as much in the medical field for the operation of continuous flux haemodialysis, for example peritoneal dialysis or plasmatic exchange with separation of the cells or the plasma, as in the industrial field in purification operations, for example in the pharmaceutical and food industries.

It should be understood that the present invention is not concerned with the structure of such a dialysis element which may be of any design and may comprise, for example hollow fibres or membranes with any passages through several dialysis chambers, the essential aspect of the process being that it is possible to modify the tonicity of the aqueous solution which is introduced into the primary compartment, due to the adjoining in the secondary compartment of an aqueous solution which is hypotonic with respect to the suspension of erythrocytes, the purpose of this, of course, being to lyse the erythrocytes.

The erythrocyte lysate must be in contact with the substance having a biological activity which is to be encapsulated, but it is possible to introduce this substance either before, or during lysis or even possibly after lysis, but in the latter case, the encapsulation yields ar not as good.

In fact, in the practical application of the process for encapsulating biologically active substances in erythrocytes, two situations may be encountered:

(a) The size of the substance to be encapsulated exceeds the pore diameter of the membrane separating the primary and secondary compartments of the dialyzer. This is the case with a macromolecular substance. Under these conditions, there is no loss of that substance during dialysis leading up to the phase of introduction of the substance into the erythrocytes and the final yield will correspond to the equilibrium phase obtained after lysis of the erythrocytes.

(b) The substance to be encapsulated is of reduced size (below 10,000 daltons) and, accordingly, will dialyze in the secondary compartment of the dialyzer during the lysis phase. This will result in a reduction in the yield of encapsulation of the substance in the erythrocytes. To reduce this loss of substance, which is highly undesirable in the case of expensive or rare compounds, the process may be modified as follows:

In effect, the erythrocytes are initially washed in a medium containing solutes of which the osmotic pressure is of the order of 220 to 300 mos. The lysis of these erythrocytes only takes place below 200 mos. It is during this phase of reduction of the osmotic pressure to 200 mos that the main loss of the substance to be encapsulated occurs if it has been introduced before the beginning of dialysis. To reduce this loss by diffusion, it is thus sufficient to introduce the substance into the medium at the beginning of lysis of the erythrocytes, i.e. when the ionic strength of the suspension has been adjusted to between 180 and 220 mos.

In this variant, before introducing the erythrocytes suspension in the first dialysis element, the ionic strength of the suspension is lowered until 180-220 mos and it is only when the osmotic strength reaches the correct value that the substance to be encapsulated is introduced. The so obtained suspension is then treated as described herein before.

Preferably, to this end, an aqueous erythrocyte suspension is continuously fed to the primary compartment of an additional dialysis element of which the secondary compartment is fed with an aqueous solution that is hypotonic in relation to the erythrocyte suspension in order to adjust the ionic strength of the primary compartment to between 180 and 220 mos.

There are several possibilities of increasing the osmotic pressure of the erythrocyte lysate when the membrane of the erythrocytes is to be resealed.

In a first process, the osmotic pressure of the erythrocyte lysate is increased by passing it into the primary circuit of a dialysis element, the secondary circuit of which contains a hypertonic solution with respect to the lysate, the solution being continuously recovered after resealing.

In a second process, the osmotic pressure of the lysate is increased by mixing it with a hypertonic and/or hyper-oncotic solution with respect to said lysate.

It should be pointed out that the product which is treated is an aqueous suspension of erythrocytes, i.e., in most cases, it is preferable to work on a "synthetic" erythrocyte suspension and not on the complete blood, i.e., a suspension which mainly contains only erythrocytes as the original blood component.

This is why, in addition to the dialysis-resealing phases, the process may preponderantly comprise the following phases:

washing and preparing the erythrocytes for lysis and resealing, washing and, optionally, resuspending the transformed erythrocytes in plasma or in an artificial composition.

Numerous known methods and variants may be added to the apparatus for encapsulating substances in red cells by the process according to the invention. The methods in question are essentially:

centrifuging to separate the cells from the plasma and for washing;

separation by means of continuous-flow or semicontinuous-flow cell separators;

using continuous-flow and semicontinuous-flow devices for separating the cells on semipermeable membranes by known methods of plasma phaeresis on membranes or hollow fibers;

washing by the same methods.

It is also well known in connection with blood transfusion that it is occasionally desirable to eliminate the white cells or the platelets before transfusion for immunological reasons or for reasons associated with the formation of microaggregates.

The same situations may be encountered in the use of lysed and resealed red globules which have encapsulated a substance of biological interest. Accordingly, it would be possible to introduce into the process an element for separating leucocytes, such as a conventional absorption filter. The other conventional processes for separating leucocytes may obviously be adapted to that element.

The use of a "synthetic" erythrocyte suspension allows the osmotic pressure of said aqueous suspension to be controlled accurately and thus ensures a good reproducibility of the results which are obtained.

When this aqueous erythrocyte suspension is being prepared, it is possible to carry out various types of "conditioning" of the suspension.

First of all, it is possible to introduce the erythrocytes into an iso-osmotic medium with respect to the blood, i.e., under natural conditions of osmotic pressure, and under these conditions, lysis will be carried out in the presence of an aqueous solution which is hypotonic with respect to the suspension of erythrocytes.

However, it is also possible to condition the erythrocytes in an aqueous solution containing substances which may diffuse through the membrane, and under these conditions, the erythrocytes will tend to swell and it will be possible to carry out lysis using an iso-osmotic medium or even, in some cases, a hyper-osmotic medium (these pressures being evaluated with respect to the normal blood osmotic pressure).

It may also be advantageous during the preparation of the synthetic erythrocyte suspension which is to be treated to add to this suspension macromolecular compounds, in particular colloids, in order to produce in this solution an oncotic pressure, and the effect of this pressure during lysis will be to restrict the loss of intracytoplasmic molecules and, in particular, the loss of haemoglobin.

Of course, it is possible to envisage, at the stage of lysis or resealing, the use not only of modifications in the osmotic pressure of the solution, but also modifications in the oncotic pressure in order to improve lysis or resealing.

A major advantage of the process according to the present invention, in addition to the possibilities of controlling the sterility and the absence of pyrogen which allows the use in man of products obtained, is that this process lends itself particularly well to a regulation by controlling the parameters, such as notably time, volume, temperature, flow rate, exchange area, conductivity and ionic strength.

The different operational parameters of the process may vary depending on the nature of the treated elements, but lysis will preferably be carried out at a temperature between 0° and 10° C. and resealing at a temperature between 20° and 40° C.

Analysis of the phenomenon of erythrocyte resealing shows that conditions different from those described in the foregoing may well be involved:

introduction of the substance to be encapsulated into the suspension of lyzed erythrocytes at 2° to 4° C. and not before entry into the dialysis circuit;

stages at different temperatures and at successive levels, leading generally to a temperature gradient of 2° to 6° C. at the beginning to between 35° and 42° C. between lysis and resealing;

introduction of resealing solutions of substances at different points of the above-mentioned levels;

variable compositions of the resealing solutions or buffers.

Finally, the encapsulation in low concentrations of highly active substances which are protein-like in character or which are readily adsorbed onto the plastic surfaces used in the process makes it appear advisable to pretreat the dialysis circuit in certain cases. These absorption phenomena are well known and, in view of the large surfaces used, may lead to the loss of a very large quantity of the substance to be encapsulated in the process. This might be the case, for example, with substances such as cytokines or enzymes. Various methods may be used for modifying the surfaces of the transformation circuits, such as for example the preliminary use of a coating based on a protein, such as albumin.

Although these methodological precautions are not directly associated with the process, they can perform a major role in its application.

As previously indicated, it has been found that although the process according to the present invention is a continuous process, yields are obtained which are widely superior to the yields observed by the said technique of a "dialysis bag". Moreover, it is possible to treat considerable volumes of blood, the treatment being carried out very rapidly.

The differences which have been observed between these results may be partly explained by the fact that the two processes are fundamentally very different. In fact, one of the processes is a kinetic method, whereas the other is an equilibrium method. Under these conditions, the considerable shortening of the period during which the red blood cells are maintained in a lysed form restricts the physicochemical membrane-medium exchanges accompanied by a loss of constituents of the erythrocyte membrane, greatly reducing the proportion of red blood cells for which lysis has become irreversible.

Of course, in addition to the advantages associated with the rapidity of treatment which can be obtained by the process, it should be mentioned that it is possible, for the dialysis phase, to treat large blood volumes, for example 200 ml of washed packed cells over a period of 10 minutes, instead of 10 to 20 ml over a period of 2½ hours by the method of a dialysis bag.

The process according to the present invention may be carried out to encapsulate a large number of substances having a biological activity. In particular, these substances are as follows:
proteins,
enzymes,
hormones,
immunomodulators,
substances generally having a pharmacological activity,
substances modifying the metabolism of erythrocytes, such as, for example allosteric effectors of haemoglobin, and
protective substances, notably cryoprotective substances of haemoglobin and erythrocytes.
nucleic acids.

As explained above, allosteric effectors of haemoglobin should be mentioned from among the substances which have a biological activity and which may be used in the present process.

Among the allosteric effectors of haemoglobin, inositol hexaphosphate (IHP) should be mentioned, but other effectors may be used, for example sugar phosphates, such as inositol pentaphosphate, inositol tetraphosphate, inositol triphosphate, inositol diphosphate and diphosphatidinylinositol diphosphate.

It is also possible to use polyphosphates, such as nucleotide triphosphates, nucleotide diphosphates, nucleotide monophosphates, alcohol phosphate esters and pyridoxal phosphate.

A whole series of natural or synthetic substances of increasing interest in cell or molecular therapy may be encapsulated, namely:
prostaglandines,
leukotrienes,
cytokinins or synthetic immunomodulators (immunoactivators of immunosuppressors). In this particular category, it may be advisable to consider using the process for modulating the immuno-defence system of the organism by means of natural or synthetic substances which can be directed by the process:
onto the reticuloendothelial system, the preferential site where erythrocytes disappear during the ageing process;
onto certain cells, such as monocytes, which are intended to be transformed into tissular macrophages, in particular by means of an antibody dependent cytolysis reaction (ADCC);
onto the lymphatic system which represents the preferential site of elimination of transfused erythrocytes, for example by the intraperitoneal route.

At the present time, the most interesting compounds are:
α, β or γ interferons or genetic recombination interferons;
interleukine II;
synthetic immunomodulators, particularly derivatives of muramyl dipeptide (MDP).

For the same reasons which are behind the selective and effective targeting of the natural or synthetic immunomodulators, apart from a retarding effect and the limitation of toxicity, it may be very useful and effective to utilize the process for encapsulating, targeting and activating substances which show anticarcinogenic properties.

Of the many other natural substances, particularly enzymes, which may be encapsulated by the process according to the invention, it is possible to give numerous examples.

Three particularly interesting examples are mentioned in the following:

(a) Encapsulation of enzymes from the metabolism of glucose

Glucose is a substrate which diffuses rapidly and freely through the membrane of the red cell.

The encapsulation of enzymes from the metabolism of glucose, particularly hexakinase, would make it possible to act on the extraerythrocytic metabolism of glucose and, hence, to modulate the concentration of blood glucose other than by the action of hormones, such as insulin.

The intraerythrocytic stability might necessitate the addition of protease inhibitors, as in the case of insulin, or other enzyme inhibitors.

(b) Encapsulation of carbonic anhydrase

The metabolism of $CO_2$ presents serious problems in the reanimation of certain patients showing a high overload of blood $CO_2$ which, hitherto, has been poorly controlled.

The encapsulation of carbonic anhydrase in more than the naturally high concentrations in the red cell would enable the equilibrium:

$$CO_2 \rightarrow CO_3H^-$$

to be displaced, the latter compound being able to be eliminated by dialysis of the blood of the patient.

(c) Encapsulation of enzymes from the metabolism of histamine

We have shown that histamine diffuses through the erythrocytic membrane in a manner similar to glucose, but kinetically more slowly.

This fundamental point enables the process to be used for encapsulating enzymes from the metabolism of histamine, more particularly diamino-oxidase (histaminase) and methyl-histamine transferase, which are the two preferential enzymes from the catabolism of histamine.

By virtue of this particular point, the process according to the invention may be considered for possible adaptation for the treatment of histamine overloads, particularly chronic histamine overloads, in allergic patients.

Without being restrictive in any way, these examples illustrate the encapsulation of enzymes capable of modifying the metabolism of certain patients suffering from acquired or congenital anomalies and the encapsulation of detoxification enzymes.

According to the invention, it is possible to target the active substance towards the macrophages, so it is very interesting to use as active substance a derivative or analog of MDP since it is known that such compound has an activity through the macrophages (C. Leclerc et L. Chedid, "Macrophage activity by synthetic muramyl peptide in lymphokines", E. Pick Ed. Academic Press Inc. 7, 1-21, 1982).

The following French patents are cited as reference for analog or derivative of MDP:
74 22909 dated 1.07.74
75 28705 dated 18.09.75
75 29624 dated 26.09.75
76 06820 dated 10.03.76
77 02646 dated 31.01.77
76 19236 dated 16.07.76
78 16793 dated 5.06.78.

Among these products, the MDP derivatives wherein the peptidic chain is mono- or di-esterified on the carboxylic group of D-glutamic acid with $C_1-C_{10}$-alkyl chains preferably $C_1$-$C_6$-alkyl, especially the butylic ester of D-glutamine, are interesting.

The mono- and di-esters having in α a $C_4$-$C_{10}$-alkyl chain, especially 4 carbon atoms, and in γ a lower $C_1$-$C_3$-alkyl chain are also especially interesting.

Of course, it is possible, if necessary and/or useful, to encapsulate simultaneously several compounds having a biological activity.

For some of these products, encapsulation allows a selective targeting on certain organs or the induction of a prolonged delay effect which may amount to from 15 to 25 days or more, according to the present data obtained in animal.

It is equally important to note that the encapsulation may induce a protective effect for some drugs which are toxic with respect to most of the tissues and organs for which the drug is not intended. the same type of activity is observed in the induction of a protective effect with respect to the drug or to the transported hormone which, in some cases, are capable of inducing an immunizing response, or when they are injected into individuals who have an antibody against these substances in the blood circulation for example an antiinsuline, antibody. This protective effect may also be exercised with respect to a metabolic deterioration in the drug or hormone.

It may be necessary to add protease inhibitor to enhance the stability of the substance in the resealed cells, such as in the case of insuline or other enzymatic inhibitors.

Finally, the process makes it possible to introduce compounds which protect haemoglobin and the membrane, enabling in particular the integrity of the erythrocytes to be protected.

The compounds in question may be cryoprotectors or lyoprotectors, the latter being particularly effective in cases of freeze-drying.

Finally, it should be noted that the erythrocytes may be frozen in the lyzed state and may be resealed on defreezing or, in cases of freeze-drying, during the rehydration phases. This latter situation makes it possible theoretically to resolve the passage of water through the membrane during re-hydration.

The present invention also relates to an apparatus intended for the encapsulation in human or animal erythrocytes of at least one substance having a biological activity, characterised in that it comprises at least the following combined elements:

a dialysis element comprising at least one primary compartment and one secondary compartment which are separated by a dialysis membrane, a device for the continuous supply of the erythrocyte suspension into the primary compartment of said dialysis element, a device which allows an aqueous solution to be introduced into the secondary compartment of the dialysis element, a device ensuring the introduction of the substance having a biological activity into the primary compartment of the dialysis element, and a device ensuring the transfer of the effluent solution from the primary compartment into a resealing assembly, comprising at least one means for increasing the osmotic and/or oncotic pressure of the effluent solution.

The structure of the dialysis element is not a characteristic of the apparatus according to the present invention, and it is possible to use any type of dialysis element, as previously indicated, within the scope of the process.

Any device, notably a pump system, and in particular peristaltic pumps which are presently used within the dialysis field may be envisaged as a continuous supply device.

The apparatus according to the present invention may include different modes of production, in particular with respect to the resealing assembly.

The first mode of production of the resealing assembly may be composed of a dialysis element comprising at least one primary compartment and one secondary compartment which are separated by a dialysis membrane, the effluent solution being introduced into the primary compartment by the transfer device and the device for increasing the osmotic pressure comprising a solution which is hypertonic with respect to the effluent solution, such hypertonic solution being contained in the secondary compartment of the dialysis element.

However, it is also possible to provide other productions of this resealing assembly which may be composed of an enclosure comprising a device for introducing a solution which is hypertonic with respect to the effluent solution.

Since lysis is preferably carried out at a fairly low temperature, between 0° and 10° C., and preferably in the region of 4° C., and since resealing is preferaly carried out at a higher temperature, for example between 20° and 40° C., the apparatus according to the present invention will preferably comprise a device for heating the suspension to be treated. This heating device may be located between the dialysis element and the resealing assembly, or directly inside the resealing assembly.

In another production, it is possible to provide after the first dialysis element a receiver which recovers all of the volume of suspension to be treated, then, after having changed the tonicity of the aqueous solution circulating in the secondary compartment of the dialysis element, it recycles the erythrocyte lysate thus obtained in the same dialysis element, and in this case, this dialysis element is used in a first step for lysis of the erythrocyte suspension, and in a second step as the resealing assembly.

The apparatus according to the present invention may also embody control circuits which, in response to modifications in characteristics of the treated suspension, will act on all of the parameters of the reaction in order to restore the characteristics of the suspension to the level of a predetermined order.

BRIEF DESCRIPTION OF THE DRAWINGS

Other characteristics and advantages of the process and the apparatus according to the present invention will be revealed in the following description of the Figures:

FIG. 10 shows the effect of the resealing temperature.

FIG. 11 shows the variation in the $p_{50}$ for various concentrations of IHP.

FIG. 12 shows the variations in various blood oxygen pressures.

FIG. 13 shows the trend of cardiac output in dependence upon the variation in the $p_{50}$.

FIG. 14 is a microphotograph of control and resealed residues.

DETAILED DESCRIPTION OF THE INVENTION

Figure 1:
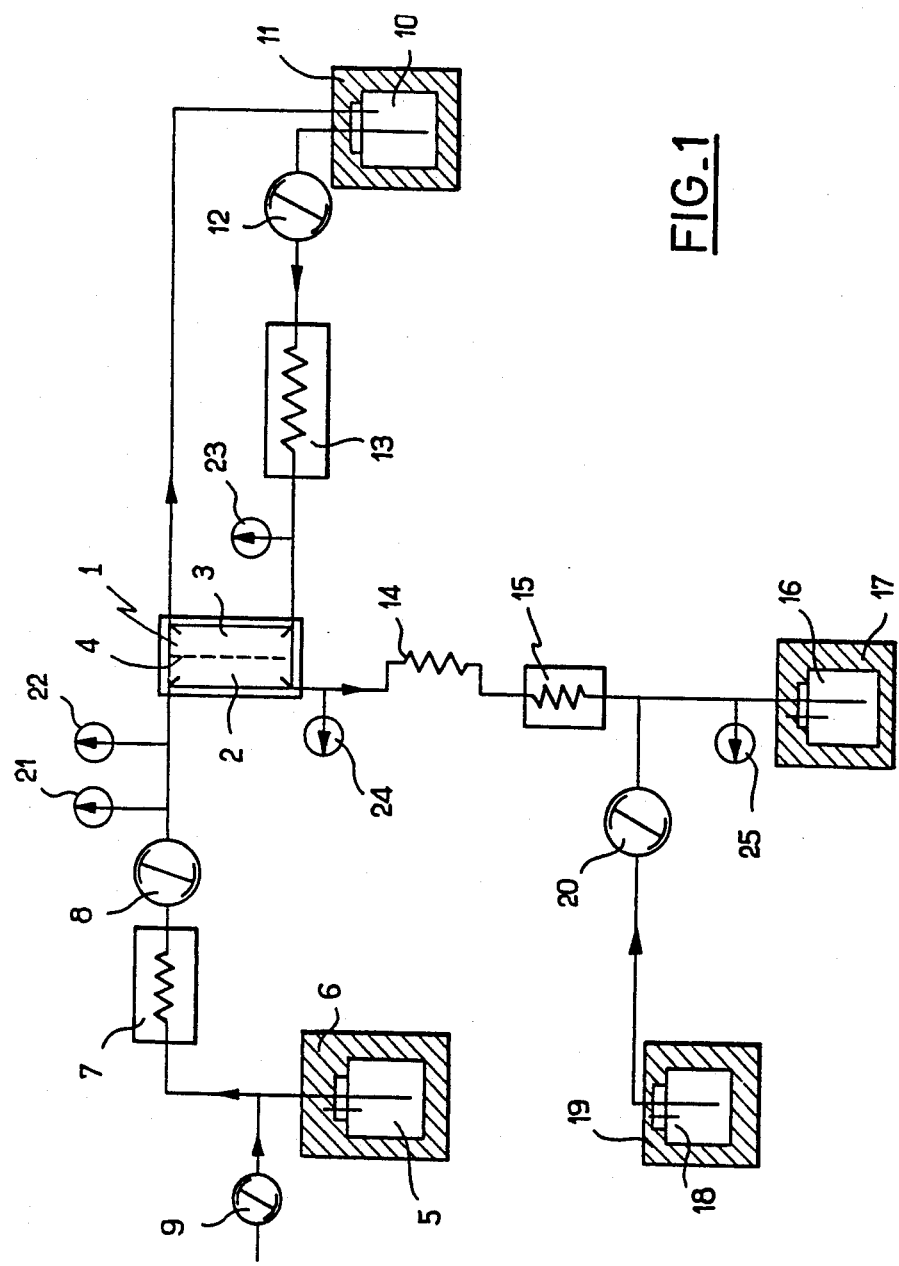
FIG. 1 shows a first embodiment of the apparatus according to the invention.

The apparatus of FIG. 1 is composed of a dialysis element 1 comprising a primary compartment 2 and a secondary compartment 3 which are separated by a dialysis membrane 4.

The primary compartment 2 is supplied with an erythrocyte suspension contained in a reservoir 5 positioned in an incubator 6.

Before being introduced into the dialyser 1, the blood is brought to the lysis temperature which is generally 4° C., by means of a heat exchanger 7.

The erythrocyte suspension is circulated by means of peristaltic pumps such as 8.

In the production which is being described, the compound having a biological activity is introduced into the circuit by means of a peristaltic pump 9 before the erythrocyte suspension penetrates into the heat exchanger 7.

The secondary compartment 3 of the dialysis element is supplied with a hypotonic solution contained in a receiver 10 which is positioned in an incubator 11. This hypotonic solution is introduced into the secondary compartment of the dialysis element by means of a peristaltic pump 12 and through a heat exchanger 13. After passing into the secondary compartment of the dialysis element, the hypotonic solution returns to the receiver 10. It may also be discarded.

In order to ensure that lysis of the erythrocytes is complete, it is possible, as illustrated in FIG. 1, to position at the outlet of the dialysis element 1 a delay line 14, i.e., usually a simple long tubing, for example.

In the most frequent case when the resealing operation has to be carried out at a temperature above the lysis temperature, a heat exchanger, such as 15 is introduced after the delay line, which exchanger will allow the lysed erythrocyte suspension to be brought to a temperature of, for example 37° C.

The lysate is continuously introduced into a receiver 16 which is contained in an incubator 17. The resealing solution which is introduced into a receiver 18 contained in an incubator 19 is added continuously, or all at once into this receiver 16 by means of a peristaltic pump 20.

When the resealing operation is complete, the erythrocyte suspension in which the compound having a biological activity is encapsulated is directly removed from the receiver 16.

One of the advantages of the apparatus according to the present invention is that it is possible to permanently control all the parameters of the reaction.

Of course, it is possible to control the temperature of the different circulating fluids by means of devices which have not been shown because they are well known from the prior art.

However, it is very advantageous to be able to control the pressure of the fluids and also their osmotic pressure in order to ensure that the exchanges will be carried out under optimum conditions.

Of course, it is unnecessary to go into details about these control devices which are known. At least one manometer such as 21 will preferably be provided to control the pressure of the fluids in the primary circuit, and an element for measuring the osmotic pressure, for example by measuring the conductivity using a device such as 22, these elements acting to modify the other parameters of the reaction, such as the feed flow rate, in order to restore the values of the pressure and the osmotic pressure to the ordered values.

It will be the same on the secondary circuit where a device denoted with reference numeral 23 will allow the pressure of the fluid as well as the osmotic pressure to be measured in order to maintain the characteristics of the fluids at certain set values.

Other control devices, such as 24 and 25 are also illustrated which ensure identical functions to those previously defined.

Figure 2:
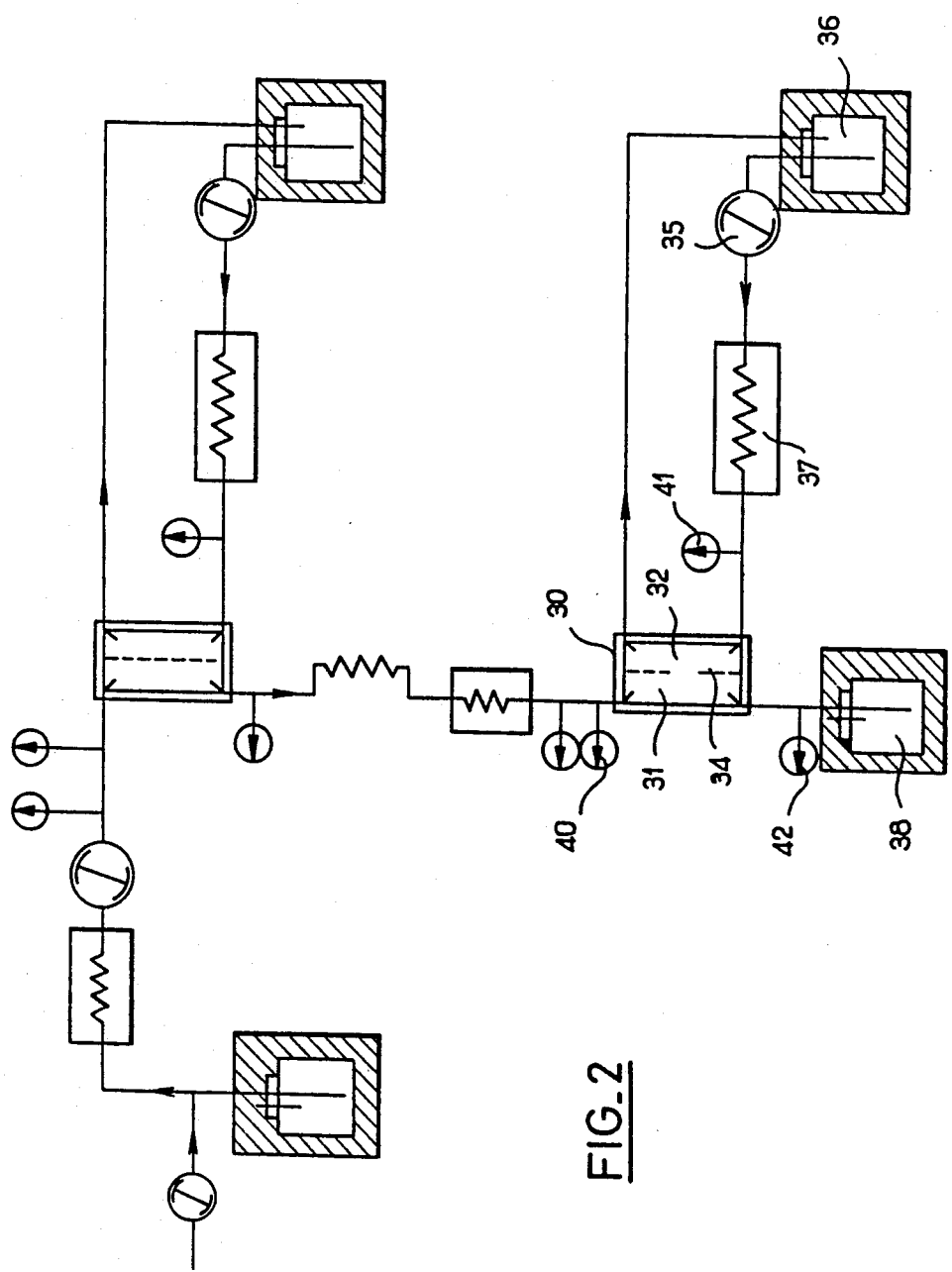
FIG. 2 shows a second embodiment of the apparatus according to the invention.

FIG. 2 illustrates an apparatus which is identical to that of FIG. 1 up to the level of the second thermal exchanger denoted with numeral 15 in FIG. 1, and since this part of the apparatus is absolutely identical to that of FIG. 1, it will not be described again.

On the other hand, the resealing stage is carried out by means of a second dialysis element 30 comprising a primary compartment 31 and a secondary compartment 32 which are separated by a dialysis membrane 34.

A hypertonic resealing solution circulates in the secondary compartment 32 by means of a peristaltic pump 35 which draws out this hypertonic solution in the receiver 36 and guides it by means of a heat exchanger 37 into the secondary compartment of the dialysis element. This hypertonic solution may be recycled in the receiver 36.

The lysis suspension originating from the first dialysis element, and after passing into the delay line and into the heat exchanger, is introduced into the primary compartment of the dialysis element 30, in which the erythrocytes are resealed, the suspension being recovered in a receiver 38 contained in an incubator, after resealing.

Here again, as previously mentioned, different control devices, such as 40, 41 and 42 are provided which allow a continuous control of the operational parameters of the process.

The flow rate of the primary circuit containing the erythrocytes is generally between 20 and 80 ml/min, whereas the flow rates of the hypertonic or hypotonic solutions of the secondary circuit are between about 100 and 1 000 ml/min.

In the tests which will be described in the following, the areas of dialysers which are used are generally about 0.41 m².

The pressures in the circuits approach 100 mm of mercury depending on the flow rates which are used.

The ionic strength of the lysis solutions is about 40 mosmoles and the ionic strength of the resealing solutions is about 300 mosmoles.

The diagram of FIG. 2 which is symmetrical for the two operations of lysis and resealing shows that it is possible to use an apparatus which only comprises a single dialysis element, and that it is possible to make it operate during a first period to lyse the erythrocyte suspension then, after having recovered all of the lysed solution, to make this dialysis system operate for the resealing operation by changing only the tonicity of the solution being supplied to the secondary compartment.

Figure 3:
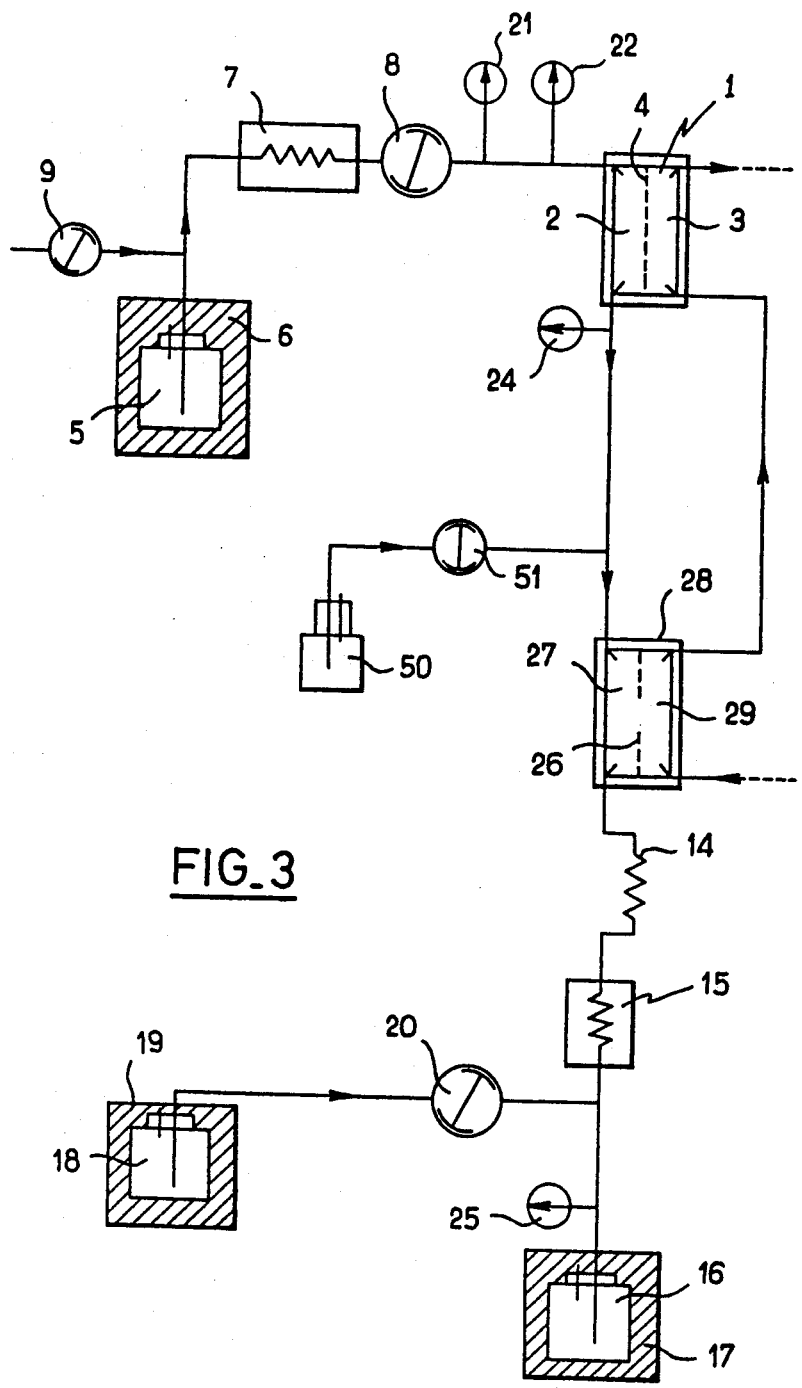
FIG. 3 shows a third embodiment of the apparatus according to the invention.

In the FIG. 3, the osmotic pressure of the erythrocyte suspension may be adjusted to 200 mos in order to limit the loss of substance to be encapsulated, as mentioned in the foregoing.

The size of the dialysis element 1 is selected in such a way that, taking the throughputs and volumes into account, the reduction in the ionic strength of the erythrocyte suspension brings the suspension to approximately 200 mos. The substance to be encapsulated which is accommodated in the container 50 is introduced by means of the pump 51 into the output circuit of the dialyzer 1 which may be formed simply by a conventional continuous throughput pressure syringe.

The erythrocyte suspension coming from the dialyzer 1 thus continuously receives the substance to be encapsulated and enters the primary circuit 27 of a dialysis element 28 of which the membrane 26 has a surface area selected in such a way that the erythrocytes entering the primary circuit undergo lysis by the initial process.

The secondary circuits 3 and 29 may be fed in series with the same hypotonic solution as shown in FIG. 1.

The ratio between the surface areas of the membranes 1 and 26 is selected to optimize the molecular exchanges in the two phases of the dialysis process.

The dialysis elements 1 and 28 may either be separated to enable existing commercial elements to be used or, alternatively, may be integrated in a two-compartment dialyzer specially adapted to the process, which may readily be achieved by means of present technology.

The outlet of the dialyzer 28 returns to the elements of the basic diagram shown in FIG. 1.

Figure 4:
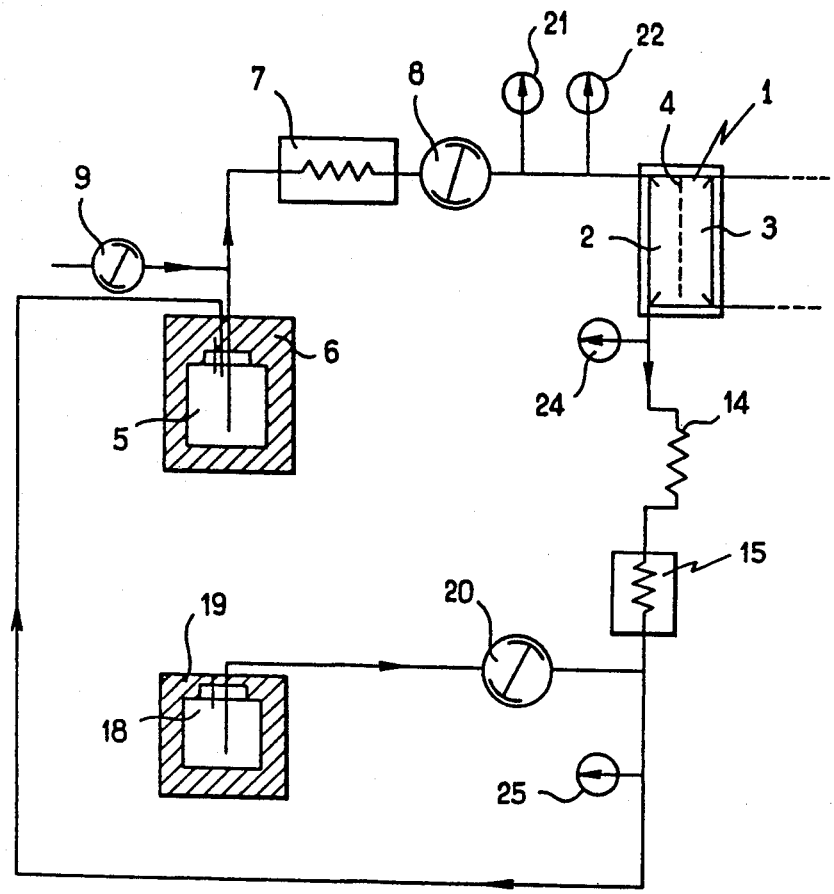
FIG. 4 shows a fourth embodiment of the apparatus according to the invention.

FIG. 4 shows one particular embodiment of the process according to the invention.

The conditions described hitherto are particularly suitable for the encapsulation of a substance in a total volume of approximately 200 to 400 ml or for the use of a continuous-flow transformation. By modifying the surface areas of the dialyzers and the throughputs, variable volumes may be treated.

However, it is useful to describe in detail a continuous recycling circuit for the extreme conditions:

(a) Unless resealing is carried out continuously, the transformation of a volume of an erythrocyte suspension amounting to several liters introduces a significant difference into the kinetics of the phenomenon between the first and last erythrocytes to pass through the phases of the dialysis process.

(b) Similarly, the handling by means of a minidialyzer of small quantities of blood (a few ml) for the encapsulation of highly active substances which do not require large volumes of blood for the doses to be administered introduces an additional parameter. This is because the effectiveness of a dialyzer depends upon its surface area and, accordingly, allows a predetermined dialysis equilibrium, although this equilibrium is only reached according to kinetics which are slower, the smaller the surface area. Accordingly, simple adaptation of throughput to surface area is not sufficient for obtaining encapsulation under suitable conditions.

In this embodiment, the surface of the dialyzer 1 is reduced and the throughput of blood through the primary circuit increased in such a way that, at the outlet end of the dialyzer 1, the osmotic pressure is only reduced for a fraction of what would be necessary for causing lysis of the red cells. The erythrocyte suspension is continuously recycled into the initial reservoir 5. The heat exchanger 15 may be programmed merely on completion of transformation. The same applies to the pump 20.

This apparatus enables the process to be carried out by successive and progressive modifications of the ionic strengths of the media which enables the kinetics of the dialyzer 1 to be ignored through the introduction of complementary kinetics associated with the volume of blood to be treated and with the throughput through the circuit.

This modification makes it possible readily to adapt the process to a very wide range of volumes of blood to be treated, taking into account the technical characteristics of currently available dialyzers, and hence, in principle, to establish the optimal encapsulation conditions for very different conditions. It is thus possible to transform both large volumes of blood and also volumes of a few ml intended for animal experimentation or for the encapsulation of a rare and expensive substance.

The apparatus which are illustrated in FIGS. 1 and 2 have been used to carry out the process which is claimed.

EXAMPLE 1

Incorporation of Desferrioxamine (Desferal)

In this Example, the apparatus which is illustrated in FIG. 1 is used.

The dialyser 1 has an area of 0.41 m$^2$ and is supplied with an erythrocyte suspension at a flow rate of 60 ml/min in the primary compartment, while a lysis solution containing $NaH_2PO_4$-$Na_2HPO_4$, pH 7.4, 10 mM, $CaCl_2$ 0.5 mM and 2 mM of glucose is introduced into the secondary compartment at a flow rate of 500 ml/min.

The erythrocyte suspension was obtained in the following manner: 5 ml of solution containing 250 mg of desferal are added to 200 ml of washed packed red blood cells, having 70% hematocrit. Lysis is carried out at 4° C. keeping the lysis suspension in a receiver 16 at this temperature for 10 minutes. 20 ml of NaCl 1.5M, containing 10% of PEG 4 000 are then introduced. The suspension is maintained in contact with this resealing solution for 30 minutes at 37° C. All of the suspension is then removed and three washing operations are carried out using NaCl at 9 g/l.

It is useful to carry out an intermediate washing operation with a solution of about 200 mos. or 250 mos. to remove some erythrocyte populations which have become fragile. Likewise, the resuspension in the initial plasma or in regeneration solutions may be necessary for good preservation of the red blood cells.

A determination shows that 148 mg of desferal (that is a gross yield of 59%) have been incorporated in the packed red blood cells, but it should be noted that 12 mg of desferal were removed in the dialysis solution, which in fact results in a net yield of desferal incorporation in the erythrocytes of 63.5%.

If the supply rate of erythrocyte suspension is modified, bringing it to 80 ml/min., the gross incorporation yield is 47.3% and the net yield is 57.9%.

With a flow rate of 40 ml/min., the gross yield is 49.4% and the net yield is 59.1%.

With a flow rate of 20 ml/min., the gross yield is 46.1% and the net yield is 64.2%.

The gross yield is calculated upon the total quantity of the product and the net yield is calculated upon the remaining product after the lysis.

These results show that there is an optimum flow rate of erythrocyte suspension for a given dialyser area, when the substance which is to be incorporated is a substance which is capable of diffusing through the dialyser membrane.

EXAMPLE 2

Incorporation of desferrioxamine (Desferal)

In this Example, the apparatus which is described in FIG. 2 is used, i.e., resealing is effected by means of a second dialysis at 22° C. using a dialysis element, such as 30.

In this case, the following resealing buffer is used: $NaH_2PO_4$—$Na_2HPO_4$ 10 mM, pH 7.4, $CaCl_2$ 0.5 mM, glucose 2 mM, NaCl 144 mM.

The other parameters are the same, and the erythrocyte suspension flow rate is 50 ml/min.

In this case, a net incorporation yield of 46.7% is observed, while the gross yield is 32.5%.

These results are easily explained, since desferal is a diffusible substance and another new quantity of desferal tends to be lost during the second dialysis.

EXAMPLE 3

Incorporation of Insulin

In this Example, insulin is encapsulated in erythrocytes by using the apparatus illustrated in FIG. 1. Only the parameters which differ from those indicated in Example 1 will be mentioned in the following.

In order to allow the insulin to be determined, the product which is used is denoted by $I^{125}$ by the chloramine T method.

10 ml of insulin (4 U/ml-432.800 cpm/ml) are added to 200 ml of packed red blood cells which have been washed three times with NaCl at 9 g/l.

The erythrocyte suspension flow rate used is 60 ml/min. After lysis, incubation is carried out for 10 minutes at 4° C.

Resealing is effected at 37° C. using 20 ml of NaCl 1.5M containing 10% of PEG 4 000.

Incubation is carried for 30 minutes at 37° C. and the red blood cells are then washed three times with NaCl at 9 g/l.

Under these conditions, the incorporation yield of the radioactivity is 48% ($\pm 4\%$). Of course, this incorporation could not foresee the biological activity of the insulin encapsulated in the red blood cells. It is well known that this hormone is modified in the presence of red blood cell haemolysate.

However, this result confirms the possibilities of incorporating a protein of 7 000 daltons in erythrocytes.

In order to preserve the functional integrity of the insulin, it may be necessary to provide the incorporation of protective substances of insulin in the erythrocyte medium, and this may of course be easily carried out using the apparatus according to the present invention.

EXAMPLE 4

Incorporation of Albumin

The process is carried out as described in Example 3, using albumin labelled by $I^{125}$. Under these conditions, a yield of about 35% is observed, and this result shows the influence of the molecular mass on the incorporation yield of a protein.

The following Examples are to illustrate the encapsulation of allosteric effectors of haemoglobin, notably inositol hexaphosphate (IHP) by the process of the present invention.

EXAMPLE 5

Incorporation of IHP

In order to produce a more or less considerable transformation of red blood cells using inositol hexaphosphate, two types of solution, for example are used which allow the ratio of IHP:Na to be varied.

Solution A 15 g of IHP 12 Na (12% $H_2O$) in 55 ml of distilled water are passed over a 400 mesh 50 W DOWEX column equilibrated in $H^+$ ions. 63 ml of acid IHP are obtained ($14.2 \times 10^{-3}$ mols).

This acid IHP is used to neutralize another solution of IHP 12 Na to pH 7.4. $38.1 \times 10^{-3}$ mols of IHP 12 Na in 153 ml are neutralized by 97 ml of acid IHP containing $17 \times 10^{-3}$ mols of IHP.

In all, a solution containing $55 \times 10^{-3}$ mols of IHP and $457 \times 10^{-3}$ mols of sodium in 250 ml is obtained. This solution is diluted to obtain a medium of 250 mosmoles/liter.

Solution B 11 g of IHP 12 Na (12% $H_2O$) are neutralized by 40 ml of N HCl in 750 ml of $H_2O$ to pH 7.4. A medium of 230 mosmoles/liter is obtained.

In this Example, the apparatus which is illustrated in FIG. 1 is used.

The dialyser 1 has an area of 0.41 $m^2$ and is supplied with an erythrocyte suspension at a flow rate which varies, depending on the tests, from 20 to 60 ml/min.

The secondary circuit is supplied at a rate of 500 ml/min with a lysis-buffer having the following composition:

$CO_3HNa$ 10 mM
$PO_4H_2K/PO_4HK_2$ 10 mM,
glucose 2 mM, pH 7.4.

The erythrocyte suspension which is used was obtained in the following manner:

An equivalent volume of one of the solutions A or B is added to 200 ml of packed red blood cells which have been washed three times with a solution of NaCl at 9 g/l (70% hematocrit).

After centrifugation, the slightly hemolyzed supernatant is discarded.

Lysis is carried out at 4° C. The lysis suspension is kept in a receiver 16 for 10 minutes at 37° C. in the presence of IHP.

The lysis suspension is resealed by adding 10% by volume of a solution containing NaCl 1.5M, PEG 4 000 at 10%.

After incubating for 30 minutes at 37° C., the red cells are washed three times with a solution of NaCl at 9 g/l and are resuspended in the original plasma.

It is useful to carry out an intermediate washing operation with a solution of about 220 mos. in order to remove some erythrocyte populations which have become fragile. Likewise, the resuspension in the initial plasma or in regeneration solutions may be necessary for good preservation of the red blood cells.

The results of these tests are provided in the following Table.

| Treatment | Control | Lysis NaCl resealed without IHP | Solution A | | | Solution B | | |
|---|---|---|---|---|---|---|---|---|
| Flow rate (ml/min) | | 60 | 60 | 40 | 20 | 60 | 40 | 20 |
| $P_{50}$ (mm Hg) | 20.6 | 19.6 | 51.5 | 66.5 | 77.0 | 36.8 | 40.7 | 46.5 |
| n of Hill 30–70% (mm Hg)$^{-1}$ | 2.40 | 2.50 | 1.64 | 1.97 | 1.25 | 1.49 | 1.53 | 1.47 |

Figure 5:
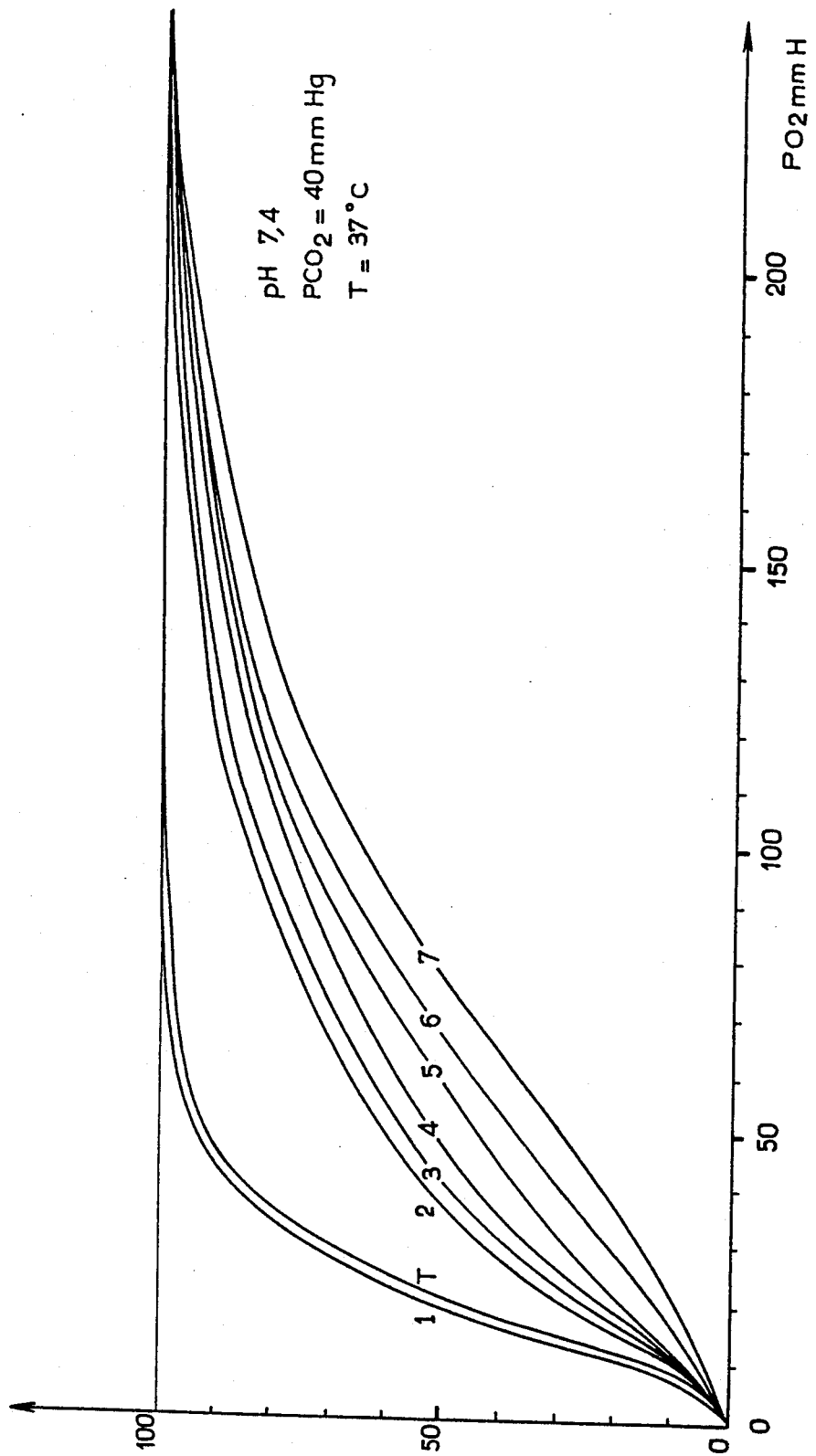
FIG. 5 shows the partial oxygen pressure as a function of the percentage of saturation of the erythrocytes.

The oxygen binding curves shown in FIG. 5 are measured at 25° C. by the rapid diffusion method using the apparatus of Duvelleroy (J. Appl. Physiol. 28, 227–233 (1970) and Tesseirre et al. (Bull. Physiopath. Resp. 11, 837–851 (1975).

The curves in FIG. 5 represent the oxygen partial pressure in mm of mercury as a function of the saturation percent of the erythrocytes for various flow rates of erythrocyte suspensions and depending on the nature of the solution which is used, A or B.

The half-saturation pressure denoted $P_{50}$ in the Table is an indication of the affinity of oxygen for haemoglobin. The slope of the curve in the vicinity of half-saturation, i.e., between 40 and 60% represents the degree of co-operation of the four fixation sites of oxygen in haemoglobin, and this slope allows the HILL coefficient to be calculated.

An improvement in the oxygen release is detected, i.e., a decrease in the affinity of haemoglobin for oxygen, either by a reduction in the HILL coefficient, i.e., a reduction in the slope of the curve of FIG. 5 in the vicinity of 50% of saturation, or by a complete displacement of the curve towards the right which corresponds to an increase in the oxygen partial pressure in the vicinity of 50% of saturation.

For the control erythrocytes of curve T, the $P_{50}$ of which is 19.3 mm of mercury, it is observed that the same erythrocytes treated by the process of the Example in the initial presence of physiological serum have a $P_{50}$ of 18.5 mm of Hg, whereas after incorporation of IHP by the process according to the present invention, the $P_{50}$ values which are observed vary between 36.8 and 77 mm of Hg depending on the flow rates which are used and on the nature of the IHP solution used.

EXAMPLE 6

Using the solution A which is diluted to obtain 210 mosmoles/liter, lysis is carried out at 4° C. at a flow rate of 20 ml/min, followed by a resealing operation lasting for 30 minutes at different temperatures. The following Table shows the influence of the resealing temperature on the $P_{50}$ value which is obtained, but also on the yield of reconstituted red blood cells which is expressed by calculating the ratio of the hematocrits of the suspensions of reconstituted red blood cells to the hematocrit of the initial suspension for a total equivalent volume.

| Resealing temperature | $P_{50}$ (mm Hg) | Yield (hematocrit) |
|---|---|---|
| 25° C. | 42 | 27% |
| 30° C. | 48 | 36% |
| 35° C. | 50.5 | 45% |
| 40° C. | 54.5 | 50% |

Figure 6:
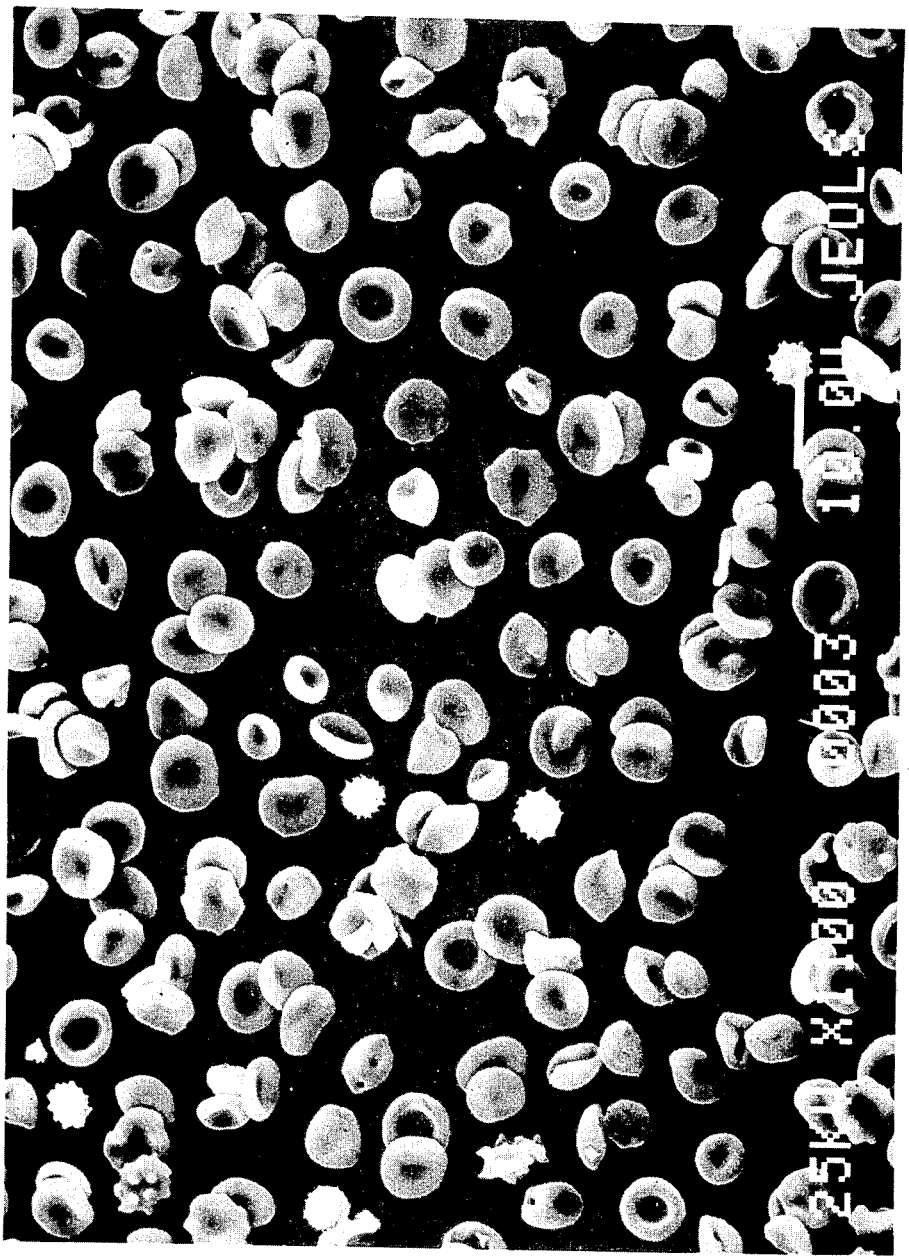
FIG. 6 is an electron microscope photograph of a resealed erythrocyte suspension.

After resealing and maintaining in a plasmatic medium, most of the red blood cells assume a discocytic shape, although slightly microcytic. The more or less vesicular forms are not significantly more numerous than in the native population. This fact is confirmed by FIG. 6 which shows a scanning electron microscope photograph of a resealed erythrocyte suspension, the $P_{50}$ of which was 68 mm of Hg.

The experimental conditions which have been described show the great possibilities of use of the continuous flow dialysis to produce, under variable conditions, the incorporation of IHP or other allosteric effectors of haemoglobin, in order to modify the oxygen-releasing properties of blood.

The control of the parameters of the reaction of lysis-resealing, volumes, flow rates, temperatures and compositions of the media may be easily carried out by means of the experimental apparatus used.

This apparatus allows the rapid transformation of large quantities of red blood cells. It could possibly be incorporated in an extra-corporeal circulation circuit. The conditions of use allow a therapeutic application in man.

The method of incorporating allosteric effectors of haemoglobin in red blood cells which is described in this patent provides a number of obvious advantages over the liposomal method described in U.S. Pat. No. 4,192,869;

(1) The method does not use exogenous phospholipids and cholesterol and thereby greatly reduces the problems of toxicity and immunological activity which have been acquired by the red blood cells.

(2) It allows a very accurate quantitation of the concentration of allosteric effectors of haemoglobin which is incorporated and consequently allows the obtention of the desired $P_{50}$ value.

(3) The incorporation process is faster and may be widely automated.

(4) The reproducibility of this method is greater than that of the liposomal method.

The following Examples carried out with Desferal using the method of Example 1 demonstrate the effect of various parameters of the process.

EXAMPLE 7

Influence of Prewashing on the Lysis Curve

As already mentioned, it is possible to swell the erythrocytes before lysis by washing them with a solution containing a substance capable of diffusing through the membrane of the red cell, such as glucose for example.

Figure 7:
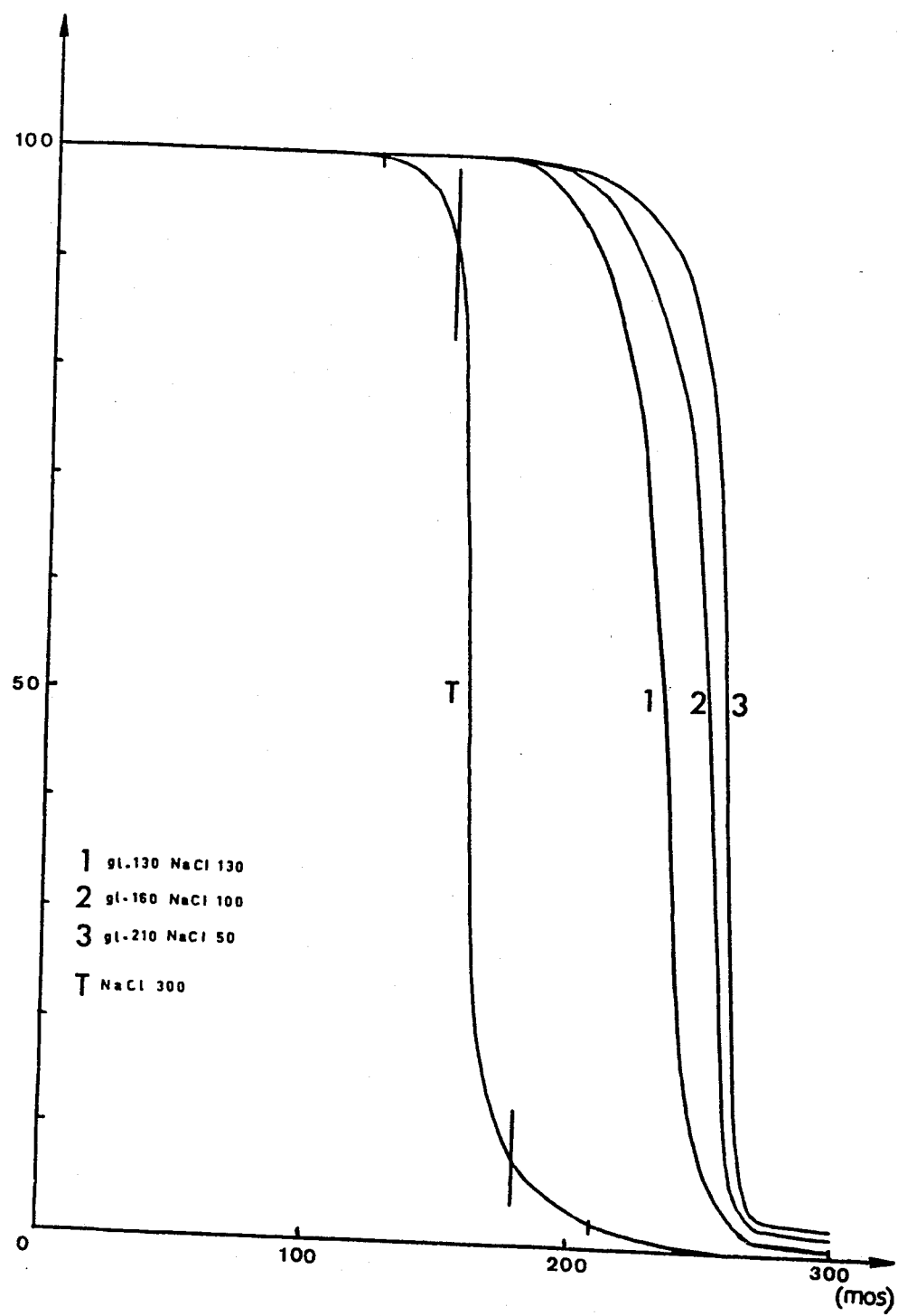
FIG. 7 shows the percentage haemolysis as a function of the osmotic pressure for various prewashes.

FIG. 7 shows the lysis curves obtained after washing in solutions containing variable proportions of glucose and sodium chloride.

| Prewashing solution (mos) | |
| --- | --- |
| 1 - 130 glycose | 130 NaCl |
| 2 - 150 glucose | 100 NaCl |
| 3 - 210 glucose | 50 NaCl |
| T - | 300 NaCl |

The curves shown in FIG. 7 clearly demonstrate the advantage of swelling the erythrocytes to improve lysis, although allowance must be made for the fact that the volume of the erythrocytes also increases. For a starting haematocrit of 70%, the extracellular volume after resealing will be greater if the mean cell volume has been artificially increased. Accordingly, these two effects are antagonistic so far as the final encapsulation yield is concerned.

Figure 8:
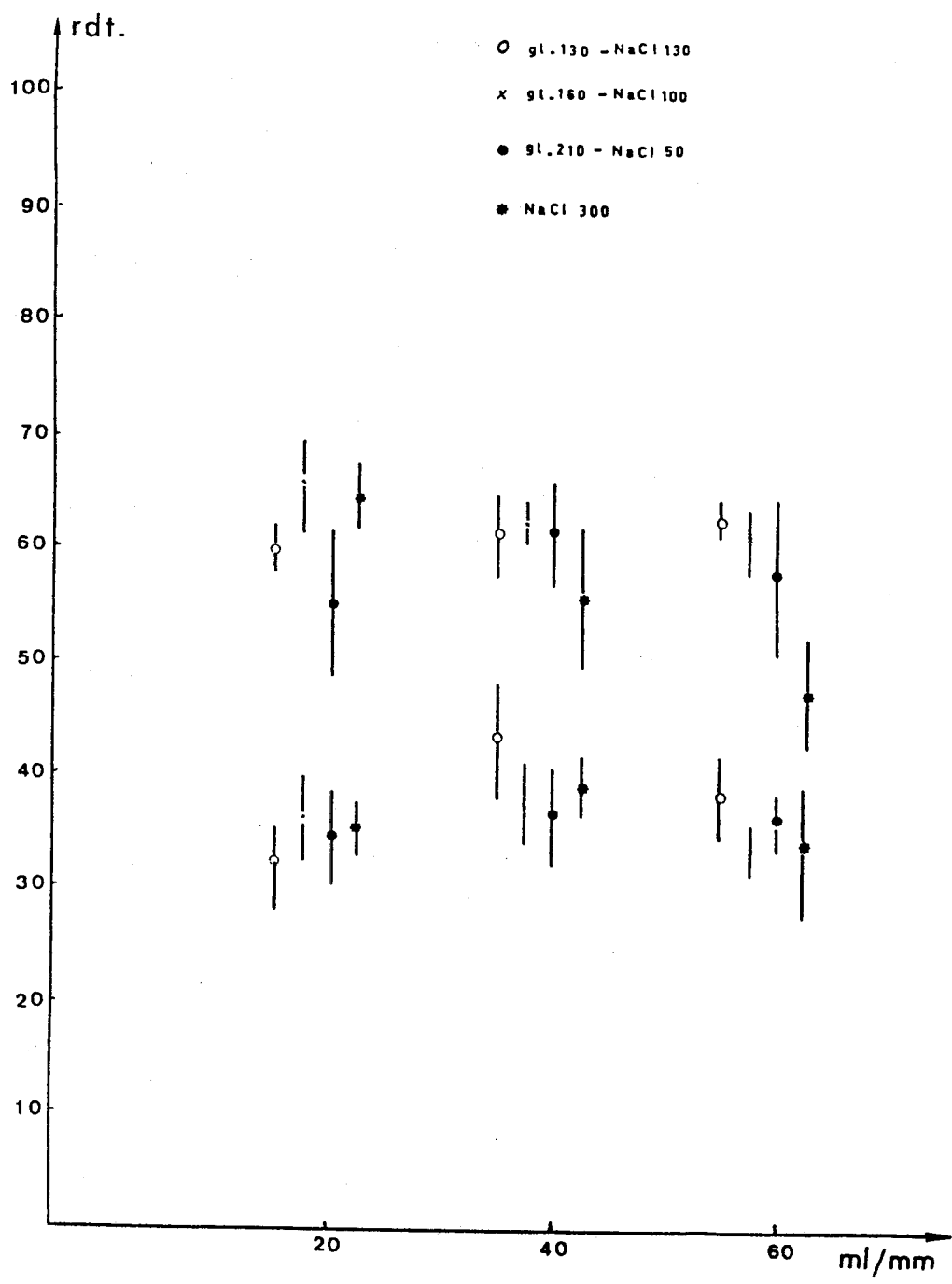
FIG. 8 shows the gross and net yields as a function of blood throughput for various prewashes.

There is thus an optimum between the prewashing conditions and the lysis conditions, as illustrated in FIG. 8.

FIG. 8 shows the net and gross encapsulation yields for various blood throughputs and for the various prewashing solutions. It can be seen that, for a given blood throughput, there is generally at least one prewash which enables the yields to be increased.

The initial results given in Example 1 for the encapsulation of Desferal were obtained using a chemical analysis technique. These results are overestimated by comparison with those obtained with the radioactive analysis technique using the complex $^{59}$Fe-desferrioxamine used for obtaining the results shown in FIG. 6.

This Example shows that it is possible by adjusting the experimental conditions to obtain results of from 40 to 50% for the gross yields.

EXAMPLE 8

Influence of the Quantity of Desferal added

In this Example, the quantity of Desferal encapsulated is measured for various concentrations of Desferal in the cell residue.

The test conditions are selected to give a gross yield of approximately 40%.

Figure 9:
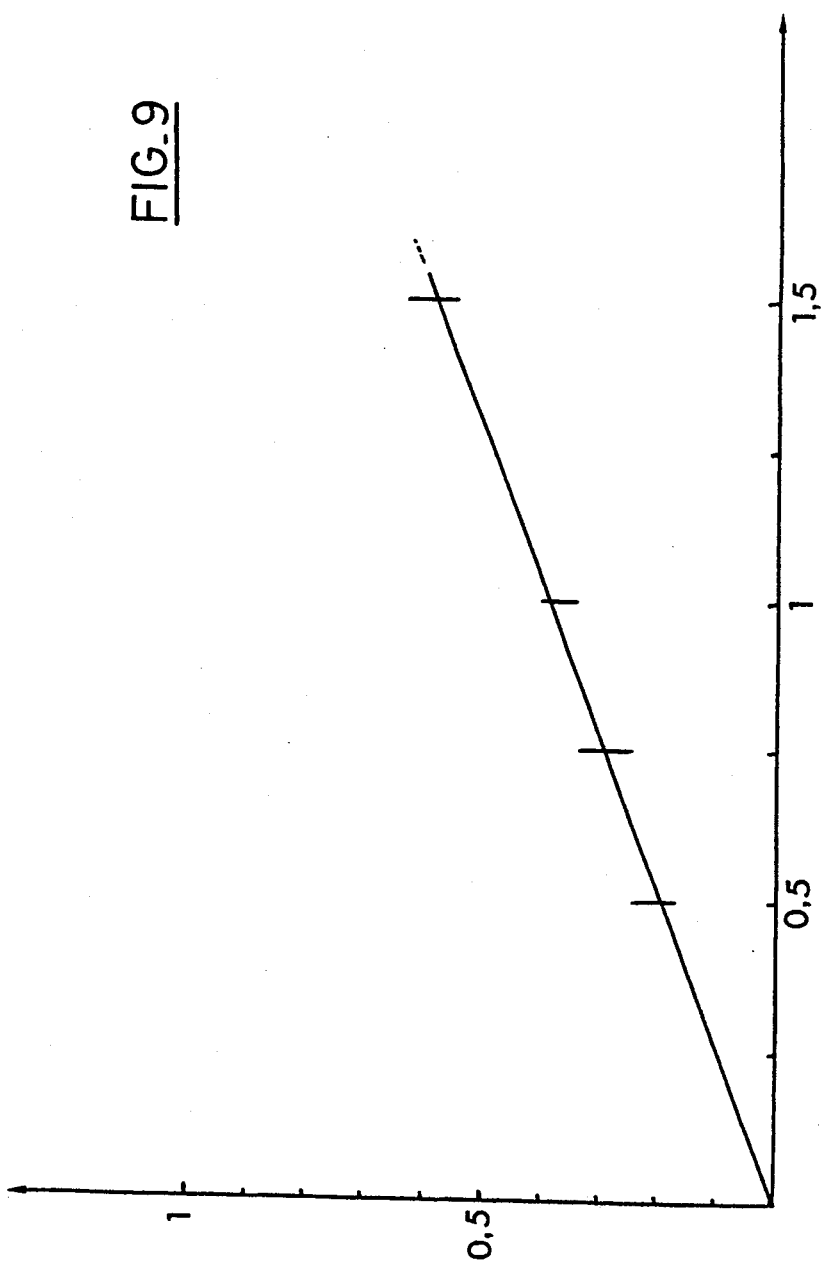
FIG. 9 shows the quantity of desferal encapsulated as a function of the initial concentration of the product.

FIG. 9 shows the results obtained and indicates the existence of a linear relation for a wide concentration range of Desferal.

It can be seen from FIG. 9 that the maximum dose of Desferal which can be encapsulated is not reached. Using the optimal conditions shown in FIG. 6 or those corresponding to the use of two dialyzers as mentioned hereinafter (yield approximately 50%), it can be seen that it is possible to encapsulate at least 800 mg to 1 g of Desferal per 100 ml of resealed red blood cells (RBC).

EXAMPLE 9

Influence of Haematocrit

The following Table shows the effect of the haematocrit of the washed RBC on the encapsulation yield

| Haematocrit % | Yield |
| --- | --- |
| 50 | 35.3 |
| 60 | 35.7 |
| 70 | 40.4 |
| 80 | 42 |

EXAMPLE 10

Influence of the Resealing Temperature

The Table in Example 6 shows the effect of the resealing temperature upon the resealing and encapsulation yield for IHP.

Complementary tests carried out with Desferal showed that, between 37° and 42° C., the effect of temperature on the final yield is fairly moderate whereas, by contrast, the lysis curves of the resealed erythrocytes are considerably modified.

FIG. 10 shows the effect of the resealing temperature upon osmotic lysis as a function of the isotonic strength of the medium.

The most stable forms are obtained in the region of 40° to 42° C. (displacement of the curves to the left). Beyond 45° C., the red cells become unstable (displacement of the curves towards the right).

EXAMPLE 11

The composition of the resealing solution used in Example 1 plays an important part, as shown in the following Table for two different erythrocytes:

| Composition of the solution | Gross yield % | Net yield % |
| --- | --- | --- |
| 1 M NaCl | 42.7–40 | 70.7–63.1 |
| 1.2 M NaCl | 38.3–39.4 | 69.1–62.9 |
| 1.5 M Nacl | 38.8–37.3 | 66.6–57.3 |
| 1 M NaCl + 10% PEG 4000 | 42.1–41.6 | 66.9–63.4 |
| 1.2 M NaCl + 10% PEG 4000 | 39.7–37.8 | 69.9–62.6 |
| 1.5 M NaCl + 10% PEG 4000 | 38.3–37.3 | 68.3–61.2 |

The dosages are made by isotopic method.

As mentioned above, it is well known that certain constituents are essential for keeping to the maximum life span of erythrocytes in vivo. This is the case with ATP, the Na/K equilibrium, $Ca^{2+}$ and $Mg^{2+}$ ions, glucose or other compounds, such as for example inosine or 2,3-DPG.

Accordingly, it may be necessary to modify the composition of resealing solution or of the washing solutions in order to maintain the biological integrity of the resealed erythrocytes intact.

EXAMPLE 12

This Example was carried out using an apparatus of the type illustrated in FIG. 3, i.e. an apparatus in which the active substance is introduced between two lysis phases of the red cells.

The following Tables show the average results obtained where this apparatus is used for the encapsulation of Desferal.

The parameters are as follows:
$S_1$ = surface area of the dialyzer 1
$S_2$ = surface area of the dialyzer 28
blood flow rate = 20, 40, 60 or 80 ml/minute
for different erythrocyte prewashing solutions;
(a) 0.15M NaCl solution (300 mos)
(b) NaCl solution, 130 mos + glucose, 130 mos.

| Flow rate ml/min | Net yield % | Gross yield % |
| --- | --- | --- |
| (a) Prewashing with NaCl, 300 mos: | | |
| $S_1 = 0.28$ m$^2$ | | $S_2 = 0.28$ m$^2$ |
| 20 | 51.9 | 38.4 |
| 40 | 38.8 | 31.6 |
| 60 | 27.7 | 24.7 |
| 80 | 19.3 | 17.7 |

-continued

| Flow rate ml/min | Net yield % | Gross yield % |
|---|---|---|
| $S_1 = 0.28\ m^2$ | | $S_2 = 0.41\ m^2$ |
| 20 | 51.6 | 32.3 |
| 40 | 39.6 | 28.7 |
| 60 | 36.6 | 28.3 |
| 80 | 38.1 | 27.5 |
| $S_1 = 0.41\ m^2$ | | $S_2 = 0.28\ m^2$ |
| 20 | 50.75 | 46.2 |
| 40 | 50.57 | 39.5 |
| 60 | 42.4 | 39.2 |
| 80 | 34.4 | 32.6 |
| (b) Prewashing with NaCl, 130 mos + glucose 130 mos: | | |
| $S_1 = 0.28\ m^2$ | | $S_2 = 0.28\ m^2$ |
| 20 | 51.8 | 46.8 |
| 40 | 52 | 45.75 |
| 60 | 48.5 | 42.1 |
| 80 | 51.5 | 45.7 |
| $S_1 = 0.28\ m^2$ | | $S_2 = 0.41\ m^2$ |
| 20 | 43.1 | 34.2 |
| 40 | 50.4 | 46.2 |
| 60 | 45.4 | 45.1 |
| 80 | 46.6 | 39.7 |
| $S_1 = 0.41\ m^2$ | | $S_2 = 0.28\ m^2$ |
| 20 | 37.45 | 27.4 |
| 40 | 38.7 | 37.7 |
| 60 | 38 | 37.8 |
| 80 | 38 | 37.15 |

The results thus obtained, compared with those shown in FIG. 8, indicate that, under certain optimal test conditions, it is possible to improve the encapsulation yield of a dialyzable substance and that these values correspond to a final yield of from 45 to 50%, depending on the red cell used. Similarly, the net and gross yield values are closer due to the reduction in the loss of dialyzable substance. Optimal conditions may be established by trial and error for different values of $S_1$ and $S_2$.

EXAMPLE 13

Influence of the age of the red cell

The tests carried out showed that there is no significant variation in the encapsulation yield when the erythrocytes used were less than 5 days. Thereafter there is a progressive and slow reduction in resealing yield.

The following Examples show the principal test results obtained with the red cells containing IHP encapsulated by the process of Example 5.

EXAMPLE 14

FIG. 11 shows the relationship obtained between the $P_{50}$-value of the saturation curve and the concentration of IHP incorporated in human red cells. The correlation coefficient is 0.916.

The curves of FIG. 12 show the changes in the saturation of haemoglobin as a function of the oxygen pressure.

A study of the curves in FIG. 12 shows that, despite a reduction in the saturation of haemoglobin for an arterial pressure of 100 mm Hg, the arteriovenous difference obtained at 30 and 40 mm is very significantly increased. These differences are very considerable for a displacement of only 10 to 20 min of the $P_{50}$-values of the saturation curves.

EXAMPLE 15

Pig cells transformed under the same conditions as the human cells of Example 14 were transfused to animals (piglets) by exsanguinotransfusion. Volumes of 300 to 500 ml reconstituted with haematocrit from the haematocrit of the animal were used in each test.

The acid-base equilibrium and the oxygenation parameters before and after transfusion are shown in the following Table:

| | Before transfusion | After transfusion |
|---|---|---|
| $P_{50}$ mmHg | 30.7 ± 1.0 | 41.2 ± 4.0*** |
| pHa | 7.36 ± 0.05 | 7.34 ± 0.04 |
| pH$\bar{v}$ | 7.33 ± 0.05 | 7.28 ± 0.05 |
| $PaCO_2$ mmHg | 39.0 ± 3.2 | 35.8 ± 5.4 |
| $PvCO_2$ mmHg | 48.1 ± 6.5 | 45.3 ± 10.5 |
| $CO_2$Ta mm/l | 23.3 ± 3.5 | 19.0 ± 4.8 |
| $CO_2$T$\bar{v}$ mm/l | 25.9 ± 3.6 | 21.3 ± 5.8 |
| Hb g/100 ml | 11.1 ± 2.0 | 11.2 ± 1.5 |

***$P < 0.001$

The transport of oxygen and the supply of oxygen to the tissues before and after transfusion are shown in the following Table:

| | Before transfusion | After transfusion |
|---|---|---|
| $PaO_2$ mmHg | 82.5 ± 10.3 | 97.5 ± 10.6* |
| $PvO_2$ mmHg | 36.7 ± 5.3 | 35.1 ± 3.7 |
| $CaO_2$ ml/100 ml | 13.9 ± 2.5 | 14.1 ± 1.5 |
| Cv $O_2$ ml/100 ml | 9.2 ± 2.9 | 5.6 ± 1.7*** |
| DAV ml/100 ml | 4.8 ± 1.1 | 7.6 ± 0.3*** |
| Q l/mn/Kg | 0.210 ± 0.029 | 0.144 ± 0.054*** |
| $VO_2$ ml/mn/Kg | 10.3 ± 1.6 | 10.6 ± 3.6 |
| Part mmHg | 91.5 ± 10.2 | 87.2 ± 22.8 |

*$P < 0.05$
***$P < 0.001$

These results show that, for a reduction in the affinity of haemoglobin for oxygen, the entire animal responds by a reduction in cardiac output and by an increase in its arteriovenous difference. The supply of oxygen to the tissues is thus increased in relation to the transport of oxygen. FIG. 13 shows the trend followed by cardiac output as a function of the $P_{50}$-value in 6 pigs exsanguinotransfused with pig cells in which variable quantities of IHP have been incorporated.

EXAMPLE 16

Characterization of the resealed erythrocytes (1) Electron microscope

FIG. 14, which is a photograph taken with an electron scan microscope, shows the comparative morphologies of the slightly echinocytic control erythrocytes and of the lyzed and resealed erythrocytes which are comparable in size. The echinocytic tendency is reduced. The cells are essentially stomatocytes of type I or II. 5% to 10% of the population is spheroechinocytic or vesicular.

(2) Haematological characteristics

FIG. 15 compares the erythrocyte volume distribution of washed and packed RB C (curve a), as measured with a Coulter S, with that measured after resealing (curve b). A slight shift in the distribution towards the microcytic forms is observed.

The following Table shows the principal characteristics of these erythrocytes.

|  | (Man) (4) | | Pig (2) | |
| --- | --- | --- | --- | --- |
|  | Control | transformed | Control | Transformed |
| Mean cell volume ($10^{-6}$ m$^3$) | 94.3 ± 4 | 84 ± 3.1 | 59 | 52.2 |
| Mean cell haemoglobin conc. (G/100 ml) | 32.3 ± 1.9 | 30 ± 2.5 | 31 | 32.2 |
| Cell distribution index | 15.4 ± 2.8 | 23.1 ± 7.2 | 21.3 | 29.2 |

It can be seen from these results that the erythrocytes lyzed and resealed by the process according to the invention are slightly microcytic and normochromic with an enlarged volume distribution towards the low values.

(3) Immunological characteristics

The lyzed and resealed erythrocytes were examined for qualitative and quantitative changes in the antigens of blood groups. The conventional methods of immunohaemotology were used, including Coombs' tests and treatment with proteolytic enzymes.

The aggregates obtained are slightly reduced in size, but are complete and perfectly visible. Accordingly, erythrocytes such as these, after transformation, may be compatibilized with regard to a potential receiver.

No significant quantitative or qualitative change was observed for erythrocytes having incorporated Desferal in the following antigen systems: ABO-Rh-CcDEe-Kk kpa kpb-MNSs-P$_1$-le$^a$-le$^b$-Fy$^a$-Fy$^b$-JK$^a$-JK$^b$-Lu$^a$.

The same applies to the following antigens: Ku-Gerbich-Fy$^3$-JK$^3$, and to the P antigens—the Cartwright and Vel antigens.

No anomaly in the polyagglutinability antigens is observed in AB serum.

These results are a clear indication of the nonmodification of the public, private or polyagglutinability antigens for the transformed erythrocytes. This result is essential to the use in vivo of these erythrocytes for transporting substances of biological interest, particularly immunomodulators which are capable of acting on the immune response of the receiver.

EXAMPLE 17

Encapsulation of MDP and its derivatives

Among the numerous synthetic or semisynthetic immunomodulators, the group of muramyl dipeptides appears particularly promising.

It has been found that some of these substances can be encapsulated by the process according to the invention.

A study has been made of their stability as a function of time in erythrocytes stored at 4° C.

100 mg of murabutide (butyl MDP) (GIRPI) in 10 ml of physiological serum are mixed with 200 ml of washed cell residue containing 70% of haematocrit. After lysis and resealing by the process of Example 2, 23 mg (23%) are found in 96 ml of washed and resealed RBC having 64% of haematocrit.

Over a period of 8 days, no significant change in the concentration of this substance in the erythrocytes stored at 4° C. is observed by HPLC analysis which signifies that this type of peptide compound is not degraded in the erythrocytes during storage, in contrast to insulin, in the absence of protease inhibitors.

Over the same period, no significant concentration of this MDP derivative is observed outside the red cells which indicates that there is no significant transmembran loss of this compound. The encapsulation yield is relatively low (23%) which may be attributed to the hydrophobic nature of the compound and to it interaction with the erythrocyte membrane.

A normal therapeutic dose of 5 mg, as currently estimated, would only necessitate about 20 ml of tranformed blood, which indicates the extreme effectiveness of this mode of transport. An operation such as this makes it possible very easily to obtain 5 useful doses spread over a given period for the same patient. In addition, this example does not in any way limit the encapsulable dose (approximately 1 g/100 ml for Desferal).

EXAMPLE 18

Encapsulation of α interferon

Following exactly the same procedure as in Example 17, a solution of purified α-interferon containing 2.1·10$^6$ units in 1 ml is mixed with 220 ml of cell residue. In view of the very low protein concentration, the dialysis circuit is incubated for 30 minutes beforehand with a 1% human albumin solution to limit the losses by nonspecific absorption in the dialysis circuit. After lysis and resealing, 840,000 units of interferon (38% yield) are found in the 125 ml of resealed and washed cell residue. It is pointed out that this yield is similar to that obtained for albumin.

Within the limits of the biological titration conducted, there is no clear reduction in the strength of the interferon over a period of 8 days at 4° C. after its encapsulation in the erythrocytes which is indicative of the excellent preservation of this compound in vivo after its encapsulation.

Encapsulation yield of the same magnitude are observed with γ interferon and interleukine II.

We claim:

1. An apparatus for the encapsulation in human or animal erythrocytes of at least one substance having a biological activity, comprising
    a first dialysis element comprising at least one first primary compartment and one first secondary compartment which are separated by a dialysis membrane,
    a means for the continuous supply of an erythrocyte suspension into the primary compartment of said dialysis element,
    a means for supplying a hypotonic aqueous solution into the secondary compartment of the dialysis element,
    a means for supplying the substance having a biological activity into the primary compartment of the dialysis element, and
    a means for transferring an effluent solution from the primary compartment into a resealing assembly, the resealing assembly comprising at least one means for increasing the osmostic and/or oncotic pressure of the effluent solution.

2. An apparatus according to claim 1, wherein the resealing assembly comprises a second dialysis element comprising at least one primary compartment and one secondary compartment which are separated by a dialysis membrane, the effluent solution being supplied into the primary compartment of said second dialysis element by the transfer means and the means for increasing the osmotic and/or oncotic pressure comprises a solution which is hypertonic with respect to the effluent solution, said hypertonic solution being supplied into the secondary compartment of said second dialysis element.

3. An apparatus according to claim 1, wherein the resealing assembly comprises an enclosure containing a means for supplying a solution which is hypertonic with respect to the effluent solution.

4. An apparatus according to claim 1, which further comprises a heating means disposed between the first dialysis element and the resealing assembly operable to heat the fluid from the first dialysis element.

5. An apparatus according to claim 1, wherein the resealing assembly is provided with a heating means to heat the fluid within the resealing assembly.

6. An apparatus according to claim 1, which further comprises a means for controlling the osmotic pressure of the erythrocyte suspension.

7. An apparatus according to claim 1, which further comprises pump means for controlling the pressure of the fluids circulating in the apparatus.

8. An apparatus as claimed in claim 1, further comprising an additional dialysis element comprising at least a second primary compartment and a second secondary compartment separated by a dialysis wall, said second primary compartment in downstream communication with said first primary compartment, and said second secondary compartment in upstream communication with said first secondary compartment.

9. An apparatus according to claim 1 further comprising a receiver, said receiver being disposed after the first dialysis element.

10. An apparatus according to claim 8, wherein peristaltic pump means moves said suspension through said primary compartments.

* * * * *